US012691113B2

(12) United States Patent
Dry et al.

(10) Patent No.: US 12,691,113 B2
(45) Date of Patent: Jul. 28, 2026

(54) THERAPEUTIC COMBINATIONS OF ACALABRUTINIB AND CAPIVASERTIB TO TREAT B-CELL MALIGNANCIES

(71) Applicant: AstraZeneca AB, Södertälje (SE)

(72) Inventors: Hannah Dry, Waltham, MA (US); Brandon Willis, Waltham, MA (US); Andrew Bloecher, Waltham, MA (US); Jerome Mettetal, Waltham, MA (US)

(73) Assignee: AstraZeneca AB, Södertälje (SE)

( * ) Notice: Subject to any disclaimer, the term of this patent is extended or adjusted under 35 U.S.C. 154(b) by 1061 days.

(21) Appl. No.: 17/755,548

(22) PCT Filed: Oct. 30, 2020

(86) PCT No.: PCT/EP2020/080493
§ 371 (c)(1),
(2) Date: May 2, 2022

(87) PCT Pub. No.: WO2021/089419
PCT Pub. Date: May 14, 2021

(65) Prior Publication Data

US 2022/0401442 A1 Dec. 22, 2022

Related U.S. Application Data

(60) Provisional application No. 62/930,208, filed on Nov. 4, 2019.

(51) Int. Cl.
*A61K 31/4985* (2006.01)
*A61K 31/519* (2006.01)

(52) U.S. Cl.
CPC ........ *A61K 31/4985* (2013.01); *A61K 31/519* (2013.01)

(58) Field of Classification Search
CPC .......................... A61K 31/4985; A61K 31/519
See application file for complete search history.

(56) References Cited

U.S. PATENT DOCUMENTS

| | | | | |
|---|---|---|---|---|
| 10,328,080 | B2 * | 6/2019 | Hamdy .................. | A61K 45/06 |
| 2017/0071962 | A1 | 3/2017 | Lannutti et al. | |
| 2018/0353512 | A1 * | 12/2018 | Collins ................ | A61K 9/2004 |

FOREIGN PATENT DOCUMENTS

| | | | | |
|---|---|---|---|---|
| WO | WO 2009/047563 | A1 | 4/2009 | |
| WO | WO 2013/010868 | A1 | 1/2013 | |
| WO | WO-2019058348 | A1 * | 3/2019 | ......... A61K 31/4985 |
| WO | 2019-211721 | A1 | 11/2019 | |
| WO | WO 2020/043787 | A1 | 3/2020 | |

OTHER PUBLICATIONS

Harrington et al. "Preclinical evaluation of the novel BTK inhibitor acalabrutinib in canine models of B-cell non-Hodgkin lymphoma." PLoS One 11, No. 7 (2016): e0159607) (Year: 2016).*

Cerulli et al. "The Bruton's Tyrosine Kinase Inhibitor CC-292 in Diffuse Large B-Cell Lymphoma (DLBCL), T-Cell Lymphoma (TCL), and Hodgkin Lymphoma (HL): Induction of Cell Death and Examination of Rational Novel/Novel Therapeutic Combinations." blood 124, No. 21 (2014): 1772 (Year: 2014).*

Harrington, Bonnie K., Heather L. Gardner, Raquel Izumi, Ahmed Hamdy, Wayne Rothbaum, Kevin R. Coombes, Todd Covey et al. "Preclinical evaluation of the novel BTK inhibitor acalabrutinib in canine models of B-cell non-Hodgkin lymphoma." PLoS One 11, No. 7 (2016): e0159607 (Year: 2016).*

Barf et al. 2017. Acalabrutinib (ACP-196): a covalent Bruton tyrosine kinase inhibitor with a differentiated selectivity and in vivo potency profile. The Journal of pharmacology and experimental therapeutics, 363(2), pp. 240-252 (Year: 2017).*

National Center for Biotechnology Information. PubChem Compound Summary for CID 25227436, Capivasertib. https://pubchem.ncbi.nlm.nih.gov/compound/Capivasertib. Accessed Jul. 10, 2025 (Year: 2025).*

Dasmahapatra et al., The Bruton tyrosine kinase (BTK) inhibitor PCI-32765 synergistically increases proteasome inhibitor activity in diffuse large-B cell lymphoma (DLBCL) and mantle cell lymphoma (MCL) cells sensitive or resistant to bortezomib, Br. J. of Haematology, 2013, 161, pp. 43-56.

Erdmann et al., Sensitivity to PI3K and AKT inhibitors is mediated by divergent molecular mechanisms in subtypes of DLBCL, Blood, 2017, 130:3, pp. 310-322.

Kosinsky et al., Quantitative Investigation of Pharmacologically Modulated Signaling and Efficacy in ABC DLBCL Using a Systems Pharmacology Model, Blood, 2019, 134, p. 5304.

Wang et al., Durable response with single-agent acalabrutinib in patients with relapsed or refractory mantle cell lymphoma, Blood Cancer Journal, 2019, 33:11, pp. 2762-2766.

Wu et al., Acalabrutinib (ACP-196): a selective second-generation BTK inhibitor, Journal of Hematology & Oncology, 2016, 9:21, pp. 1-4.

International Search Report and Written Opinion for PCT/EP2020/080493 dated Jan. 27, 2021.

Foucquier et al., "Analysis of drug combinations: current methodological landscape," *Pharmacol. Res. Perspect.* 3(3) (Jun. 2015) (Hoboken, New Jersey, US).

(Continued)

*Primary Examiner* — James H Alstrum-Acevedo
*Assistant Examiner* — Carolyn L. Ladd
(74) *Attorney, Agent, or Firm* — Arnold & Porter Kaye Scholer LLP

(57) ABSTRACT

The present disclosure relates to therapeutic combinations of acalabrutinib and capivasertib, or pharmaceutically acceptable salts thereof, for treating, preventing, partially alleviating, or ameliorating a B-cell malignancy, such as non-Hodgkin's lymphoma, in a subject in need thereof. The present disclosure also relates to pharmaceutical compositions comprising acalabrutinib and capivasertib. The present disclosure also relates to kits comprising acalabrutinib and capivasertib.

22 Claims, 9 Drawing Sheets

(56) References Cited

OTHER PUBLICATIONS

Keith et al., “Multicomponent therapeutics for networked systems,” *Nat. Rev. Drug. Discov.* 4,71-78 (2005) (Baden-Wuerttemberg, Germany).
Kapadia et al., “PARK2 Regulates eIF4B-Driven Lymphomagenesis,” Mol Cancer Res 20(5), 735-748 (2022).
Lehár et al., “Chemical combination effects predict connectivity in biological systems,” *Mol. Syst. Biol.* 3:80 (2007) (Baden-Wuerttemberg, Germany).
Phelan et al., “A Multiprotein Supercomplex Controlling Oncogenic Signaling in Lymphoma,” Nature 560(7718):387-391 (2018).
Wu et al., “Epstein-Barr virus (EBV) provides survival factors to EBV+ diffuse large B-cell lymphoma (DLBCL) lines and modulates cytokine induced specific chemotaxis in EBV+ DLBCL,” *Immunology* 152:562-573 (2017).

* cited by examiner

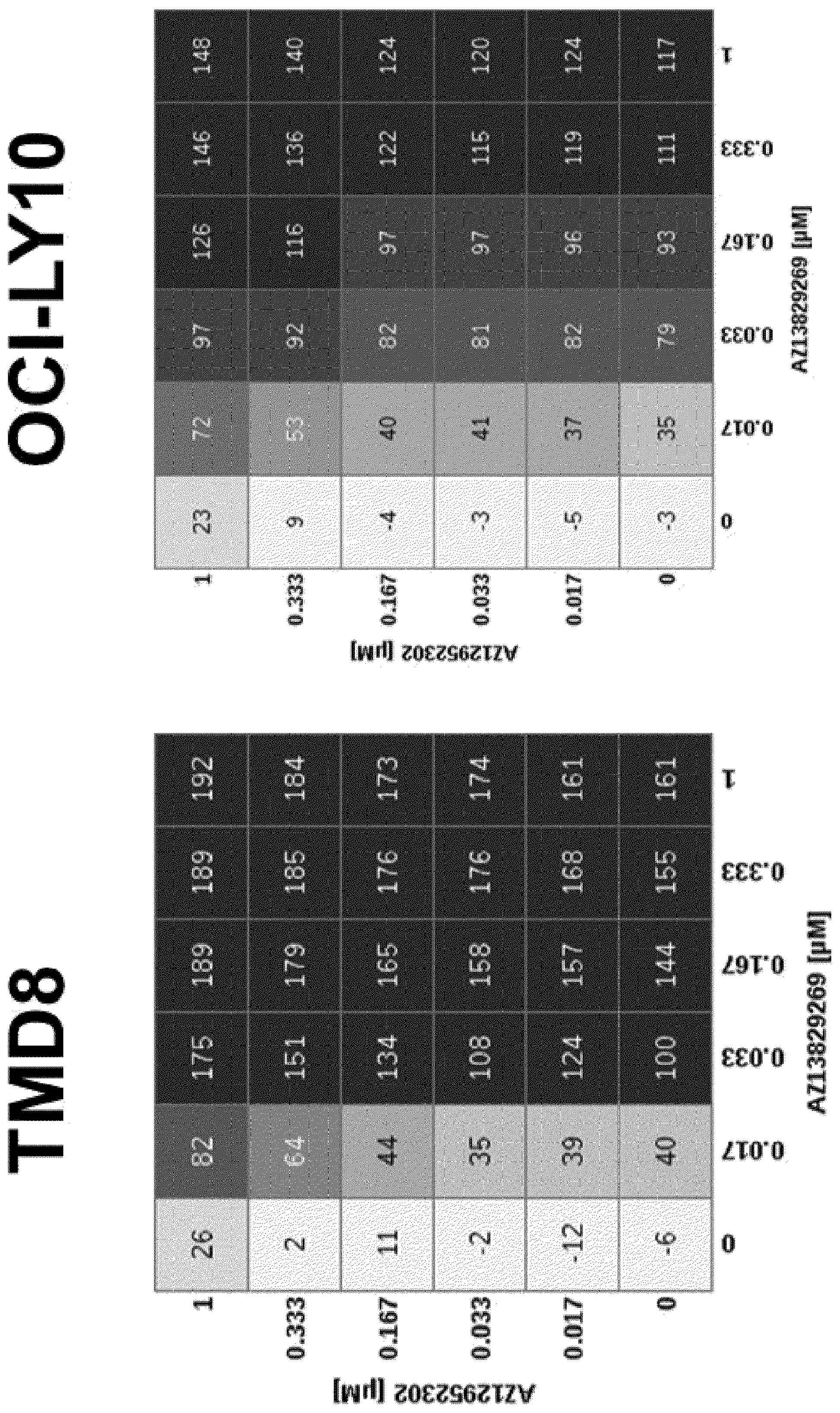
FIG. 1: COMBINATION SIGNAL HEATMAPS FOR TMD8 AND OCI-LY10 CELLS

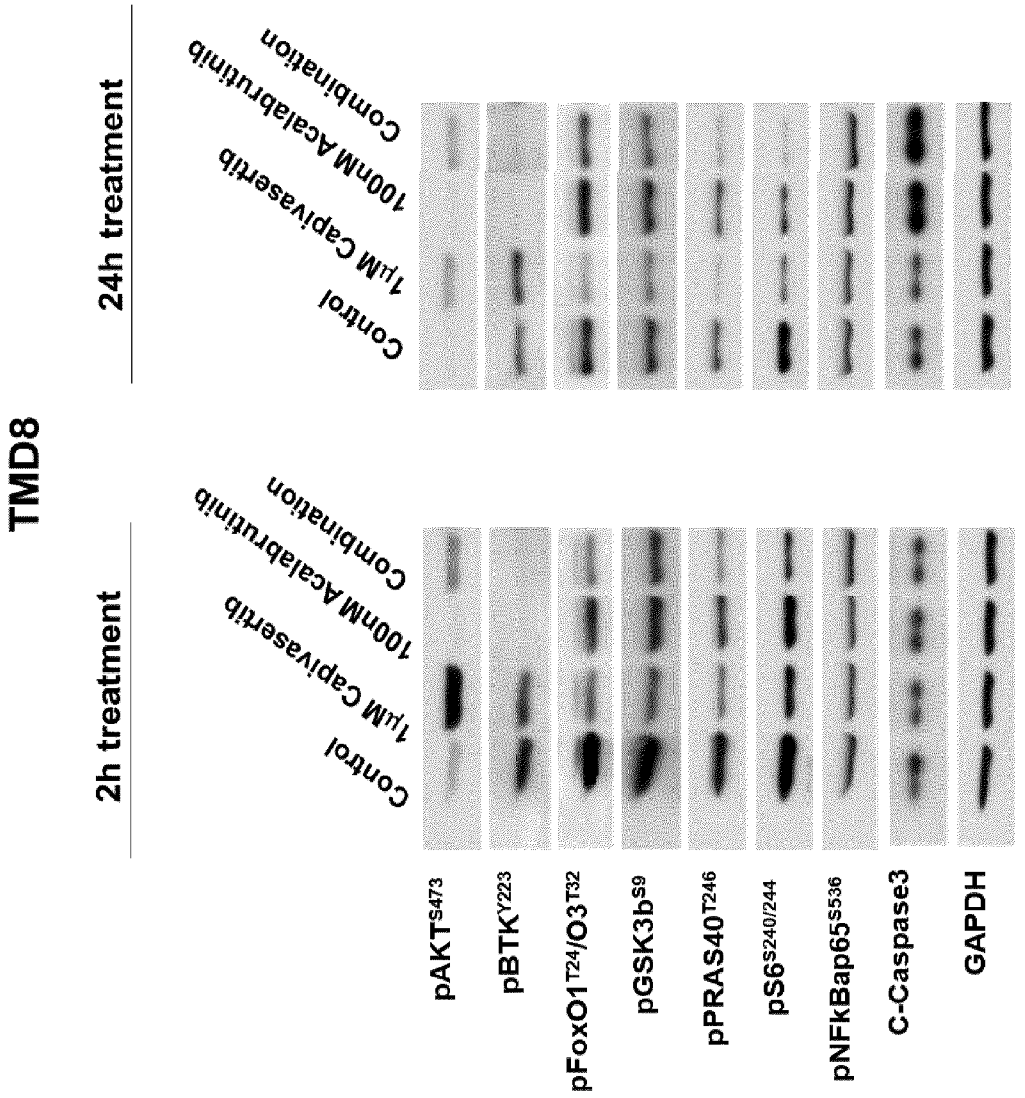
FIG. 2A: WESTERN BLOTS FOR TMD8 CELLS

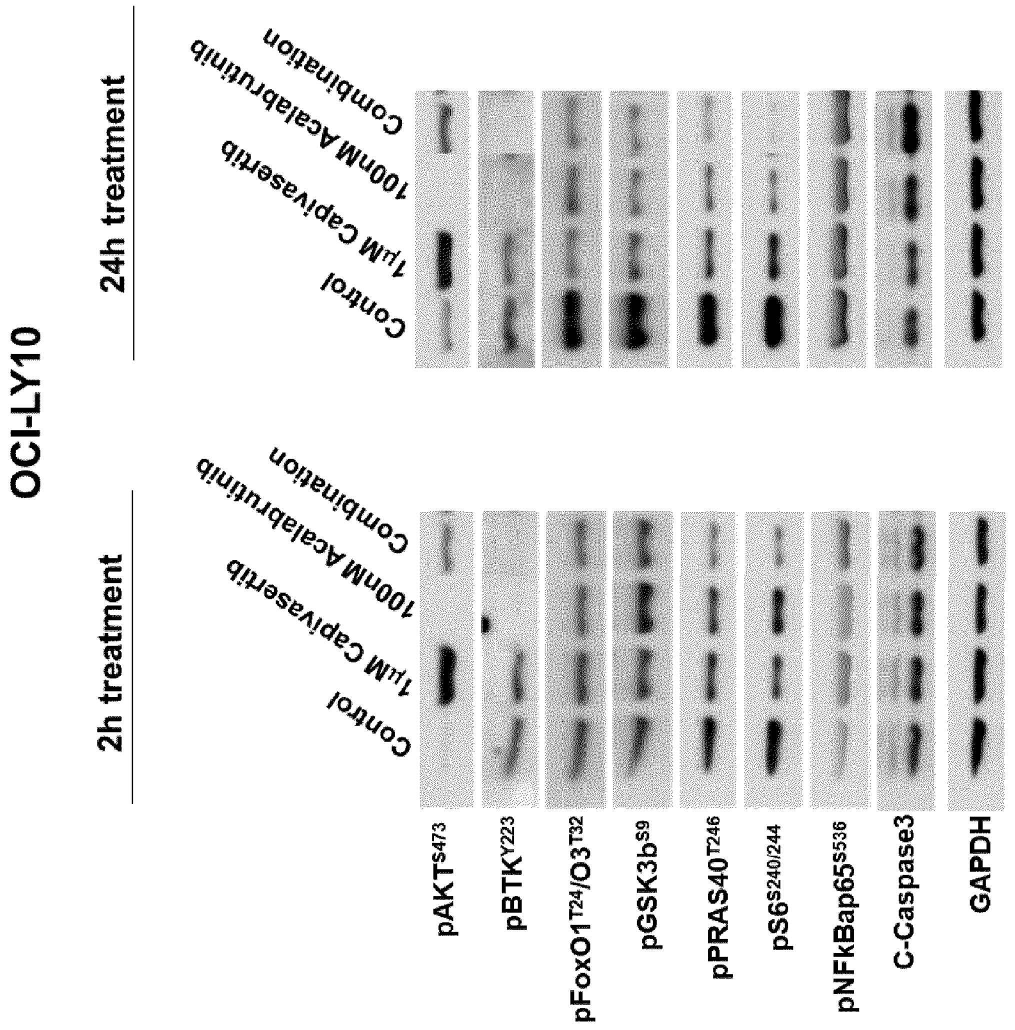
FIG. 2B: WESTERN BLOT FOR OCI-LY10 CELL

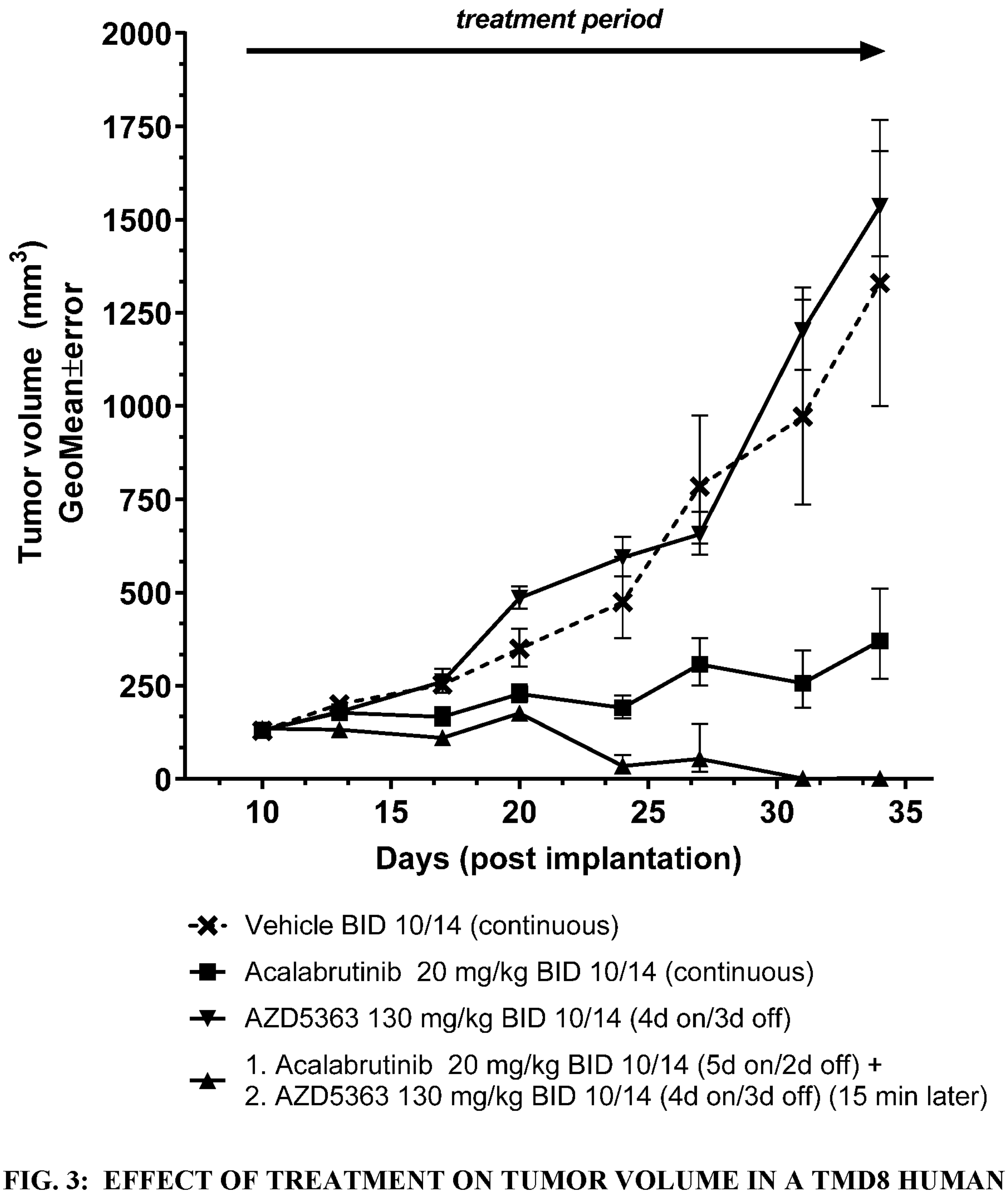
FIG. 3: EFFECT OF TREATMENT ON TUMOR VOLUME IN A TMD8 HUMAN ABC DLBCL XENOGRAFT MOUSE MODEL

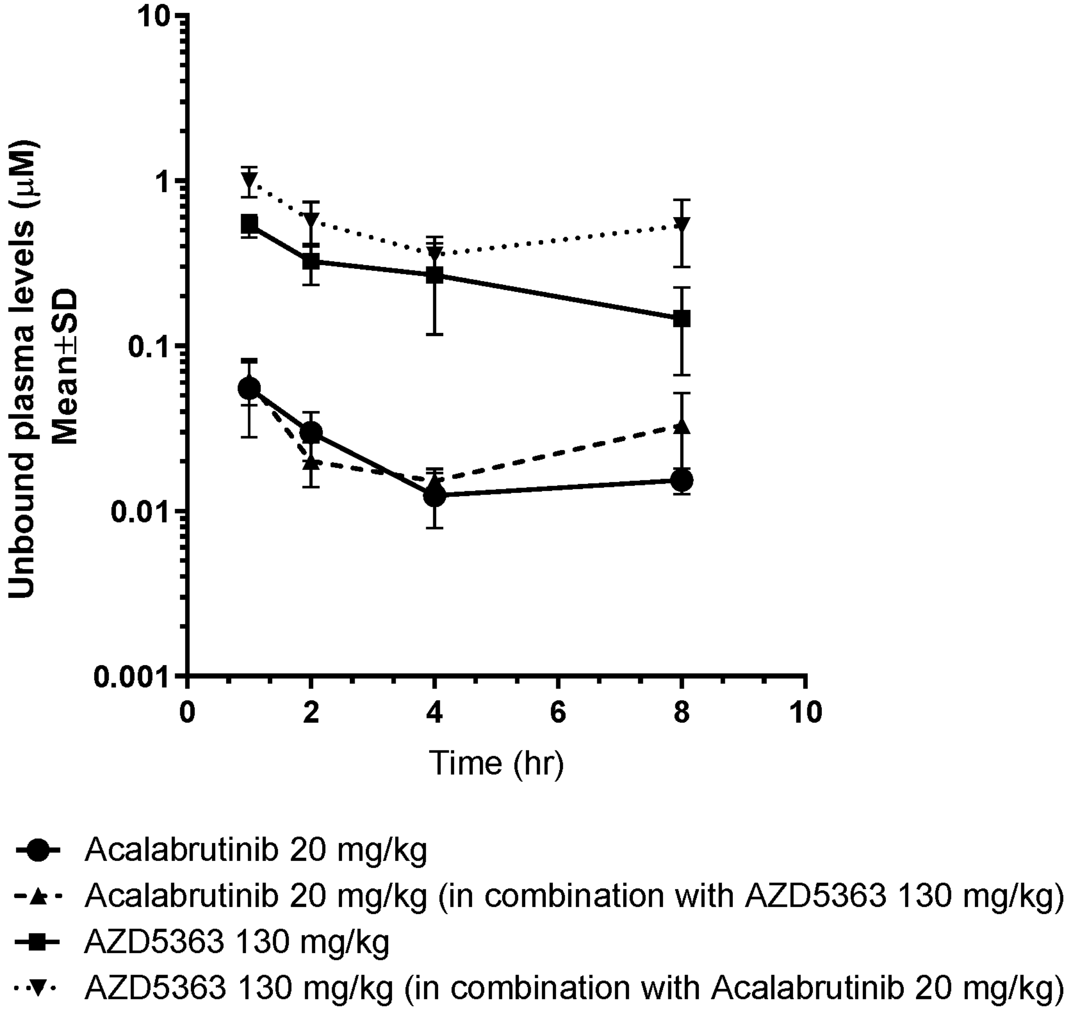
FIG. 4: STEADY STATE DRUG EXPOSURE LEVELS IN A TMD8 HUMAN ABC DLBCL XENOGRAFT MOUSE MODEL AFTER TREATMENT

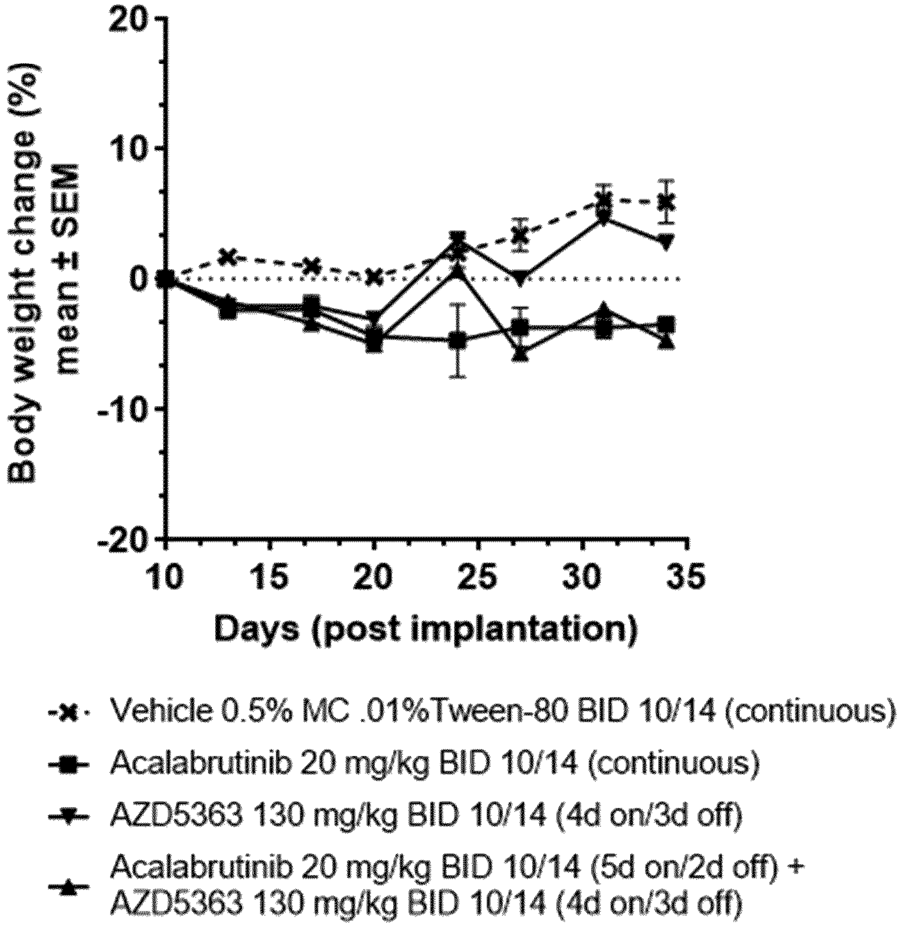
FIG. 5: EFFECT OF TREATMENT ON BODY WEIGHT IN A TMD8 HUMAN ABC DLBCL XENOGRAFT MOUSE MODEL

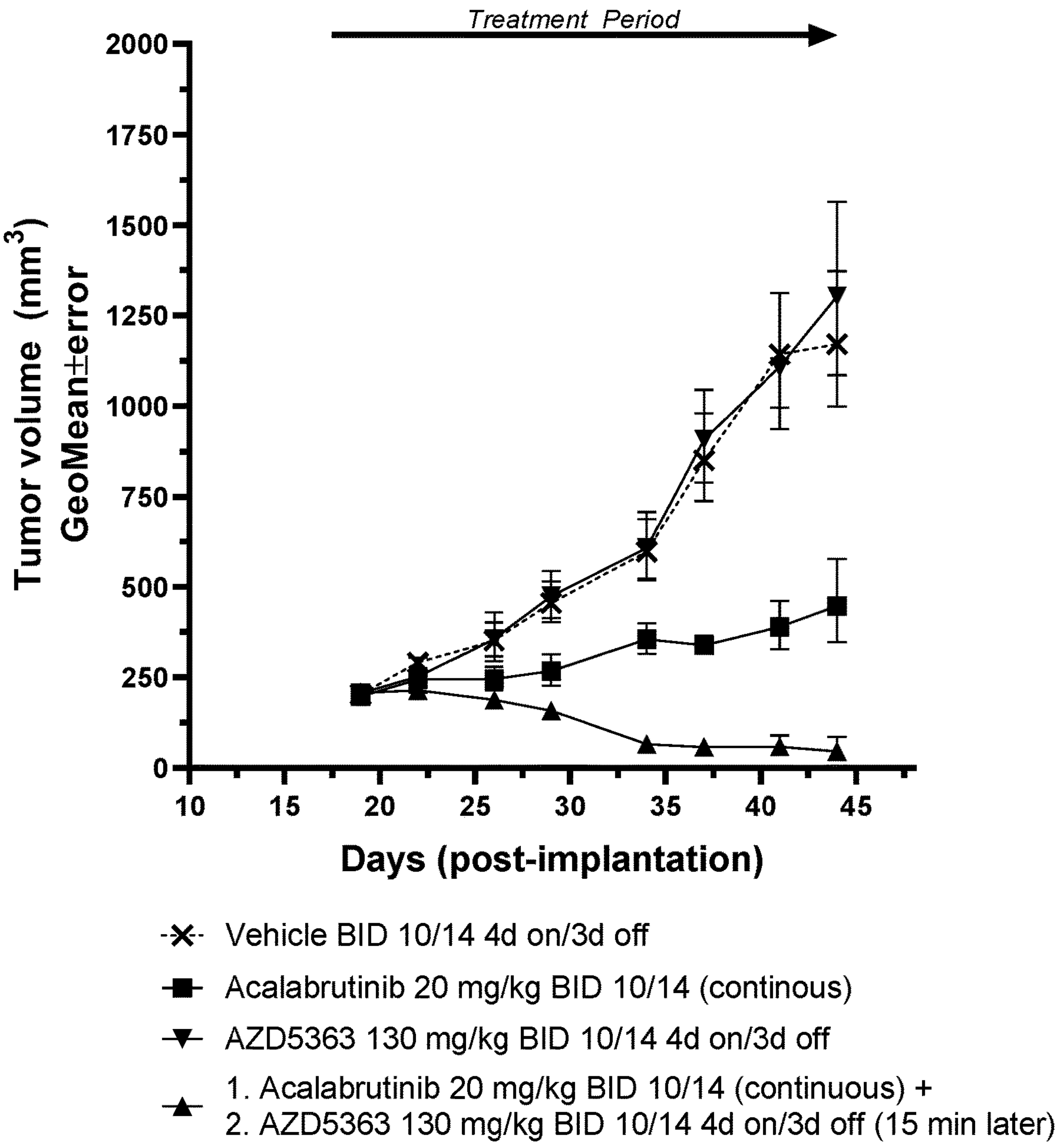
FIG. 6: EFFECT OF TREATMENT ON TUMOR VOLUME IN A OCI-ly10 HUMAN ABC DLBCL XENOGRAFT MOUSE MODEL

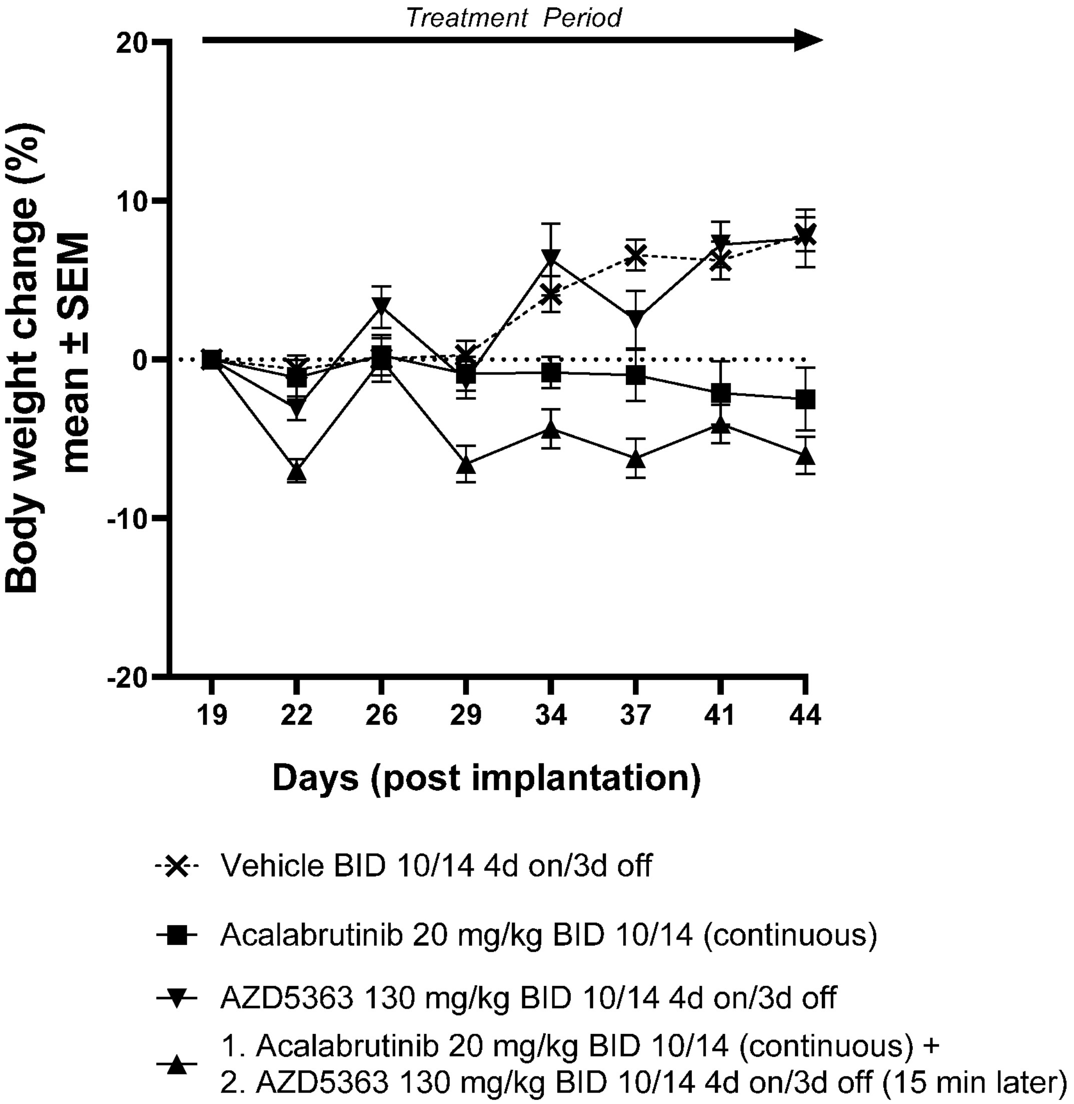
FIG. 7: EFFECT OF TREATMENT ON BODY WEIGHT IN A TMD8 HUMAN ABC DLBCL XENOGRAFT MOUSE MODEL

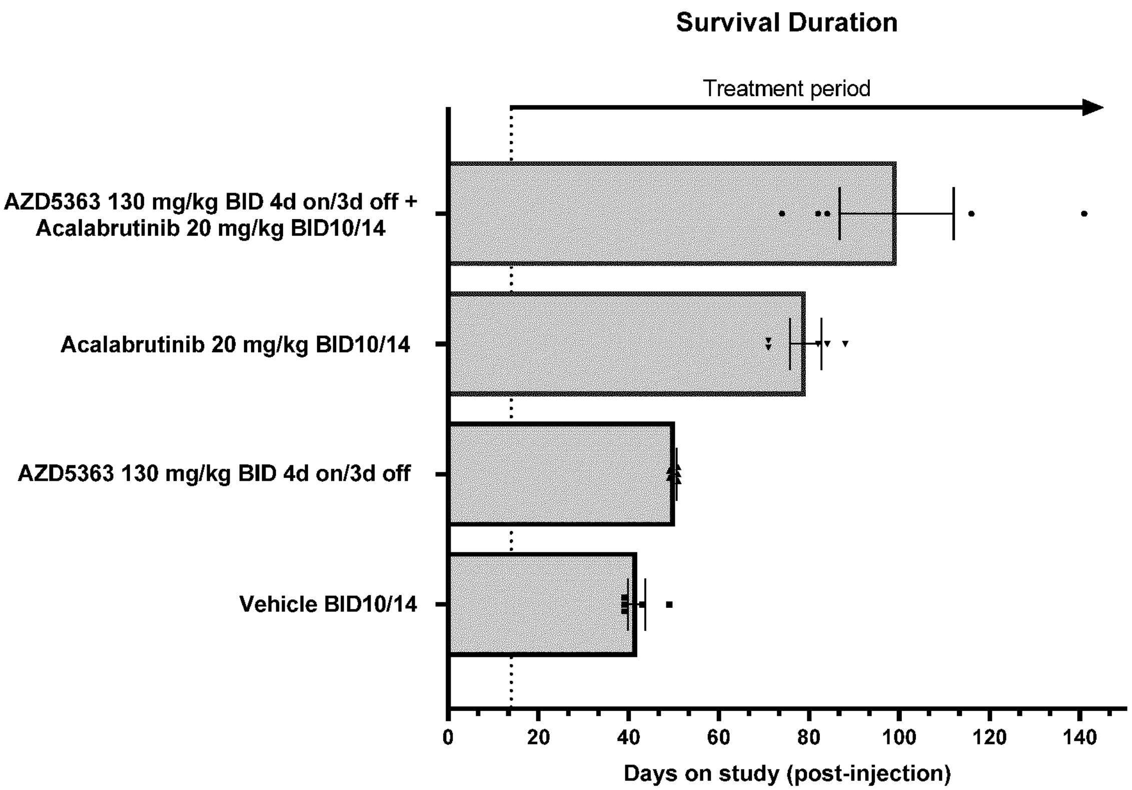
FIG. 8: EFFECT OF TREATMENT ON SURVIVAL DURATION IN A DISSEMINATED TMD8-LUC2 HUMAN ABC DLBCL XENOGRAFT MOUSE MODEL

THERAPEUTIC COMBINATIONS OF ACALABRUTINIB AND CAPIVASERTIB TO TREAT B-CELL MALIGNANCIES

CROSS-REFERENCE TO RELATED APPLICATIONS

This application is a U.S. National Stage Application of International Application No. PCT/EP2020/080493, filed on Oct. 30, 2020, which claims the benefit under 35 U.S.C. § 119(e) of U.S. Provisional Application No. 62/930,208, filed Nov. 4, 2019. Each of the above listed applications is incorporated by reference in its entirety for all purposes.

FIELD OF THE INVENTION

The present disclosure relates, in general, to therapeutic combinations of acalabrutinib and capivasertib, methods of treatment with combinations of acalabrutinib and capivasertib, pharmaceutical compositions comprising acalabrutinib and capivasertib, and kits comprising acalabrutinib and capivasertib.

BACKGROUND OF THE INVENTION

The B-cell antigen receptor (BCR) is implicated in the pathogenesis of several B-cell malignancies, including diffuse large B-cell diffuse lymphoma, follicular lymphoma, mantle cell lymphoma, and B-cell chronic lymphocytic leukemia. Bruton Tyrosine Kinase (BTK) is an essential kinase downstream of the BCR signalling complex. Acalabrutinib (also known as ACP-196 and by the chemical name of 4-{8-amino-3-[(2S)-1-(but-2-ynoyl)pyrrolidin-2-yl]imidazo[1,5-a]pyrazin-1-yl}-N-(pyridin-2-yl)benzamide) is a selective, covalent BTK inhibitor that is the active pharmaceutical ingredient in the drug product CALQUENCE®. CALQUENCE® is FDA approved for the treatment of adults with relapsed or refractory mantle cell lymphoma, chronic lymphocytic leukemia, and small lymphocytic leukemia, and is currently being evaluated in clinical trials for the treatment of other indications, including Waldenström's macroglobulinemia.

AKT is a serine/threonine-specific protein kinase that plays a key role in multiple cellular processes such as glucose metabolism, apoptosis, cell proliferation, transcription, and cell migration. Mammalian cells express three closely related AKT isoforms that are encoded by different genes: AKT1 (protein kinase Bα), AKT2 (protein kinase Bβ), and AKT3 (protein kinase Bγ). Capivasertib (also known as AZD5363 and by the chemical name of (S)-4-amino-N-(1-(4-chlorophenyl)-3-hydroxypropyl)-1-(7H-pyrrolo[2,3-d]pyrimidin-4-yl)piperidine-4-carboxamide) is a selective inhibitor of all three AKT isoforms. Capivasertib currently is being evaluated in clinical studies for use in treating cancers including breast cancer and prostate cancer.

Non-Hodgkin lymphoma represents a broad spectrum of diseases arising from lymphocytes "frozen" at various stages of development. Although understanding of the biology and genetics of non-Hodgkin lymphoma has increased in recent years, few impactful or curative therapies have emerged for the treatment of relapsed/refractory or aggressive non-Hodgkin lymphoma. There currently remains a high unmet medical need due to the disease-associated morbidity and mortality of non-Hodgkin lymphoma and the few efficacious treatment options.

The present disclosure relates to the unexpected finding that a combination of acalabrutinib and capivasertib can provide an efficacious therapeutic option for treating B-cell malignancies such as non-Hodgkin lymphoma, particularly in the treatment of diffuse large B-cell lymphoma (DLBCL) as described below.

BRIEF DESCRIPTION OF THE INVENTION

In one aspect, the disclosure relates to therapeutic combinations for simultaneous, separate, or sequential administration, wherein the combination comprises a compound of Formula I:

(I)

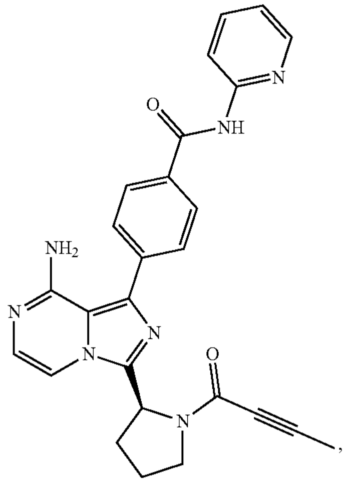

or a pharmaceutically acceptable salt thereof, and a compound of Formula II:

(II)

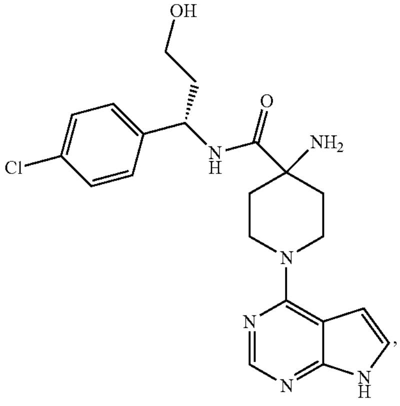

or a pharmaceutically acceptable salt thereof.

In another aspect, the present disclosure relates to methods of treating a B-cell malignancy in a subject in need thereof, comprising administering to the subject a first amount of a compound of Formula I:

(I)

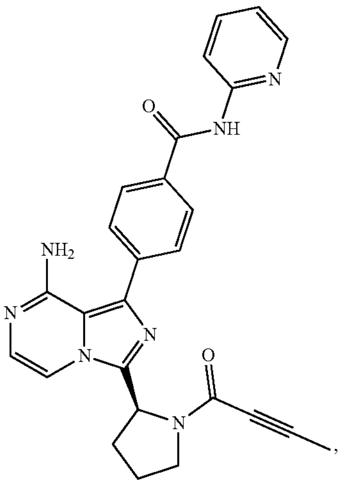

or a pharmaceutically acceptable salt thereof, and a second amount of a compound of Formula II:

(II)

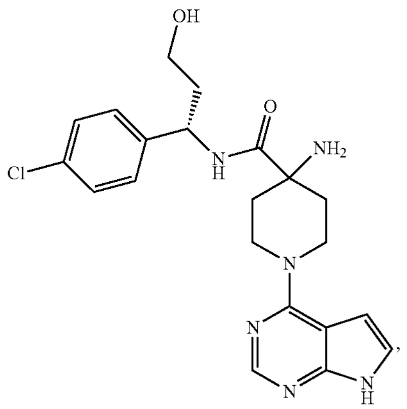

or a pharmaceutically acceptable salt thereof, wherein the first amount and the second amount together comprise a therapeutically effective amount.

In another aspect, the present disclosure relates to pharmaceutical compositions comprising:

a compound of Formula I:

(I)

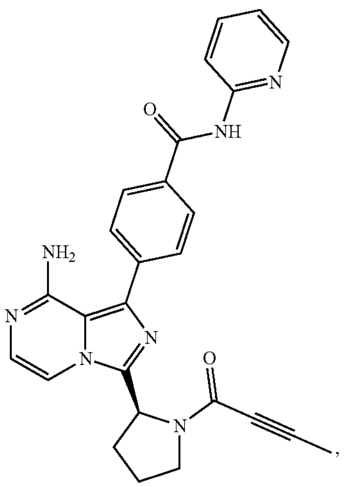

or a pharmaceutically acceptable salt thereof;

a compound of Formula II:

(II)

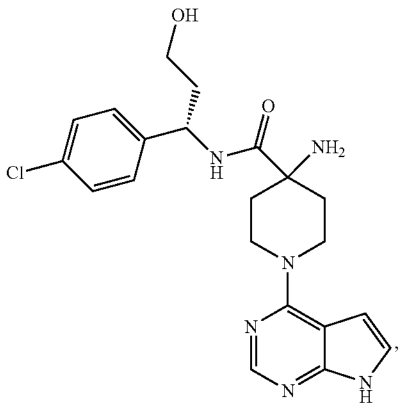

or a pharmaceutically acceptable salt thereof; and a pharmaceutically acceptable carrier.

In another aspect, the present disclosure relates to kits comprising:

a compound of Formula I:

(I)

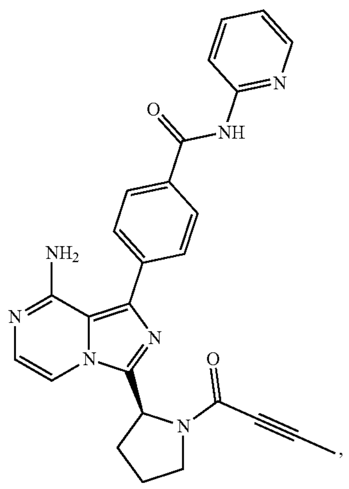

or a pharmaceutically acceptable salt thereof, and a compound of Formula II:

(II)

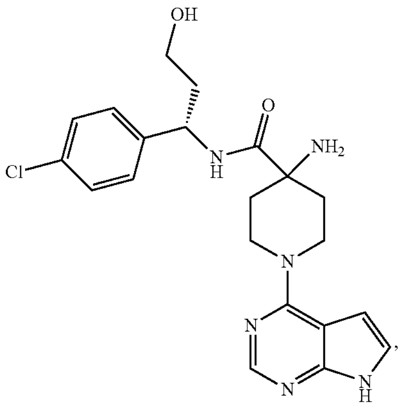

or a pharmaceutically acceptable salt thereof.

BRIEF DESCRIPTION OF THE DRAWINGS

FIG. 1 illustrates Combination Signal Heatmaps (% inhibition of growth signal) for TMD8 cells and OCI-LY10 cells after treatment with a combination of acalabrutinib and capivasertib for 72 hours.

FIGS. 2A and 2B illustrate western blots for TMD8 cells and OCI-LY10 cells, respectively, after treatment with acalabrutinib, capivasertib, or a combination of acalabrutinib and capivasertib for 2 hours or 24 hours.

FIG. 3 illustrates the effect of treatment with acalabrutinib, capivasertib, or a combination of acalabrutinib and capivasertib on tumor volume in a TMD8 human ABC DLBCL xenograft mouse model.

FIG. 4 illustrates the steady state drug exposure levels for acalabrutinib and capivasertib in a TMD8 human ABC DLBCL xenograft mouse model after treatment with acalabrutinib, capivasertib, or a combination of acalabrutinib and capivasertib.

FIG. 5 illustrates the effect of treatment with acalabrutinib, capivasertib, or a combination of acalabrutinib and capivasertib on body weight in a TMD8 human ABC DLBCL xenograft mouse model.

FIG. 6 illustrates the effect of treatment with acalabrutinib, capivasertib, or a combination of acalabrutinib and capivasertib on tumor volume in an OCI-ly10 human ABC DLBCL xenograft mouse model.

FIG. 7 illustrates the effect of treatment with acalabrutinib, capivasertib, or a combination of acalabrutinib and capivasertib on body weight in an OCI-ly10 human ABC DLBCL xenograft mouse model.

FIG. 8 illustrates the effect of treatment with acalabrutinib, capivasertib, or a combination of acalabrutinib and capivasertib on survival duration in a disseminated TMD8-luc2 human ABC DLBCL xenograft mouse model.

DETAILED DESCRIPTION OF THE INVENTION

I. Definitions

Unless defined otherwise, all technical and scientific terms used herein have the same meaning as is commonly understood by one of skill in the art to which this invention belongs.

The term "combination" can refer to simultaneous, separate, or sequential administration of two or more agents. In one aspect, "combination" can refer to simultaneous administration (e.g., administration of both agents in a single dosage form). In another aspect, "combination" refers to separate administration (e.g., administration of both agents in separate dosage forms, but at substantially the same time). In a further aspect of the invention, "combination" refers to sequential administration (e.g., where a first agent is administered, followed by a delay, followed by administration of a second or further agent). Where the administration is sequential or separate, the delay in administering the later component should be neither too long nor too short, so as not to lose the benefit of the combination.

The terms "co-administration," "in combination with," "simultaneous," and "concurrent," as used herein, encompass administration of two or more active pharmaceutical ingredients to a subject and include simultaneous administration in separate compositions, administration at different times in separate compositions, or administration in a composition in which two or more active pharmaceutical ingredients are present.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "treat," "treating," and "treatment" refer to at least partially alleviating, inhibiting, preventing and/or ameliorating a condition, disorder, or disease, such as B-cell malignancies. The terms "treatment of B-cell malignancies" includes both in vitro and in vivo treatments, including in warm-blooded animals such as humans. The effectiveness of treatment of B-cell malignancies can be assessed in a variety of ways, including but not limited to: inhibiting cancer cell proliferation (including the reversal of cancer growth); promoting cancer cell death (e.g., by promoting apoptosis or another cell death mechanism); improvement in symptoms; duration of response to the treatment; delay in progression of disease; and prolonging survival. Treatments can also be assessed with regard to the nature and extent of side effects associated with the treatment. Furthermore, effectiveness can be assessed with regard to biomarkers, such as levels of expression or phosphorylation of proteins known to be associated with particular biological phenomena. Other assessments of effectiveness are known to those of skill in the art.

The term "QD" means quaque die, once a day, or once daily.

The term "BID" means bis in die, twice a day, or twice daily.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Examples include isopropylamine, trimethylamine, diethylamine, triethylamine, tripropylamine, and ethanolamine.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

When ranges are used herein to describe, for example, dosage amounts, all combinations and sub-combinations of ranges and specific embodiments therein are intended to be included.

Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

As used in this application, the amount of a compound refers to the amount of that compound in its free base form.

The abbreviations listed in Table 1 below have the meanings indicated in that table.

TABLE 1

| ABBREVIATION | MEANING |
|---|---|
| ABC | Activated B Cell |
| ABC DLBCL | Activated B Cell Diffuse Large B-Cell Lymphoma |
| AKT | Protein Kinase B |
| BCR | B-cell antigen receptor |
| BKT | Bruton Tyrosine Kinase |
| CR | Complete Response |
| DLBCL | Diffuse Large B-Cell Lymphoma |
| DLT | Dose-Limiting Toxicity |
| DMSO | Dimethyl Sulfoxide |
| DOR | Duration of Response |
| FDA | United States Food and Drug Administration |
| GCB | Germinal Center B Cell |
| GCB DLBCL | Germinal Center B Cell Diffuse Large B-Cell Lymphoma |
| MC | Methylcellulose |
| mg | Milligram(s) |
| mg/kg | Milligrams/Kilogram |
| μl | Microliter |
| μM | Micromolar |
| NHL | Non-Hodgkin Lymphoma |
| nM | Nanomolar |
| ORR | Overall Response Rate (CR + PR), |
| OS | Overall Survival |
| PDX | Patient-Derived Xenograft |
| PFS | Progression-Free Survival |
| PK | Pharmacokinetic(s) |
| PTEN | Phosphatase and Tensin Homolog Protein |
| R/R | Relapsed/Refractory |
| SCID | Severely Combined Immunodeficient |
| SDS | Sodium Dodecyl Sulfate |
| S6 | Ribosomal protein S6 |
| TGI | Tumor Growth Inhibition |

For clarity, Table 2 below summarizes the compound identifier, chemical name, and structure used interchangeably throughout this application with respect to each compound discussed.

TABLE 2

| COMPOUND IDENTIFIER | NAME | STRUCTURE |
|---|---|---|
| Compound 1 | 4-{8-amino-3-[(2S)-1-(but-2-ynoyl)-pyrrolidin-2-yl]-imidazo[1,5-a]pyrazin-1-yl}-N-(pyridin-2-yl)benzamide (i.e., ACP196, AZ13829269, or acalabrutinib) | 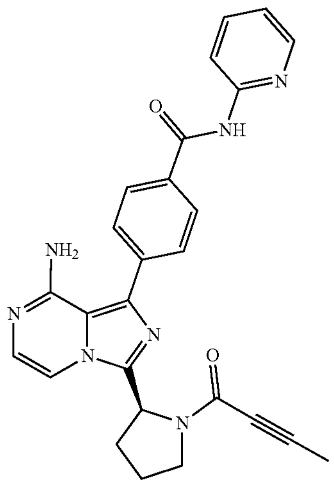 [SMILES: CC#CC(=O)N1CCC[C@H]1c1nc(-c2ccc(C(=O)Nc3ccccn3)cc2)c2c(N)nccn12] |
| Compound II | (S)-4-amino-N-(1-(4-chlorophenyl)-3-hydroxypropyl)-1-(7H-pyrrolo[2,3-d]pyrimidin-4-yl)piperidine-4-carboxamide (i.e., AZD5363, AZ12952302, or capivasertib) | 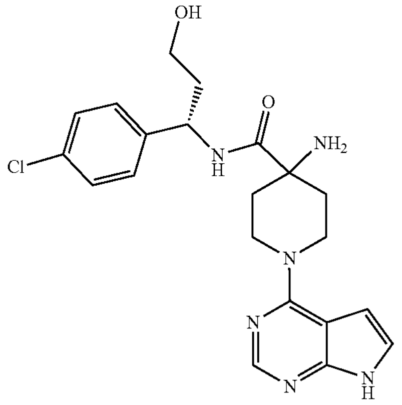 [SMILES: NC1(C(=O)N[C@@H](CCO)c2ccc(Cl)cc2)CCN(c2ncnc3[nH]ccc23)CC1] |

II. Therapeutic Combinations, Methods of Treatment, and Uses

The present disclosure relates, in part, to therapeutic combinations and corresponding methods for the treatment of B-cell malignancies, including non-Hodgkin lymphomas such as diffuse large B-cell lymphoma. In particular, the present disclosure relates to methods of treatment comprising administration of a therapeutic combination of acalabrutinib, or a pharmaceutically acceptable salt thereof, and capivasertib, or a pharmaceutically acceptable salt thereof, to a subject in need thereof, particularly a human subject in need thereof, to treat a B-cell malignancy.

It has been found that therapeutic combinations of acalabrutinib, or a pharmaceutically acceptable salt thereof, and capivasertib, or a pharmaceutically acceptable salt thereof, can be more effective than either agent alone in the treatment of B-cell malignancies. In some embodiments, the combinations and methods of treatment discussed below exhibit synergistic effects that may result in greater efficacy, decreased side effects, the use of less active pharmaceutical ingredient to achieve a given clinical result, or other synergistic effects. Such combinations can provide enhanced efficacy by, for example, promoting cancer cell death, inhibiting cancer growth (e.g., inhibiting an increase in tumor volume), and/or increasing duration of response.

As reflected in the study results described later in the Examples, the combination of capivasertib and acalabrutinib has broader and greater activity in diffuse large B-cell lymphoma than either agent alone. Acalabrutinib has shown single agent activity in several diffuse large B-cell lymphoma cell lines, particularly those classified as activated B-cell (ABC) subtype. In contrast, capivasertib has shown single agent activity in several diffuse large B-cell lymphoma cell lines, particularly those classified as germinal center B-cell (GCB) subtype and having PTEN loss. The combination of capivasertib and acalabrutinib, however, has shown broader and greater activity than either agent alone, for example, in a xenograft model of DLBCL using the TMD8 cell line, which is an activated B-cell (ABC) subtype that is not PTEN deficient. Such activity for the combination cannot be explained simply by addition of the single agent activities of capivasertib and acalabrutinib.

Although this specification primarily discusses acalabrutinib and capivasertib combinations, therapeutic combinations and methods of treatment comprising the administration of additional therapeutic agents (triple combinations, etc.) to further enhance the treatment are also within the scope of this disclosure.

Accordingly, in one embodiment, the present disclosure relates to therapeutic combinations for simultaneous, separate, or sequential administration, wherein the combination comprises a compound of Formula I:

(I)

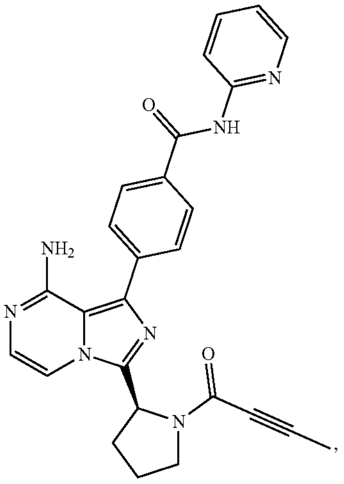

or a pharmaceutically acceptable salt thereof, and a compound of Formula II:

(II)

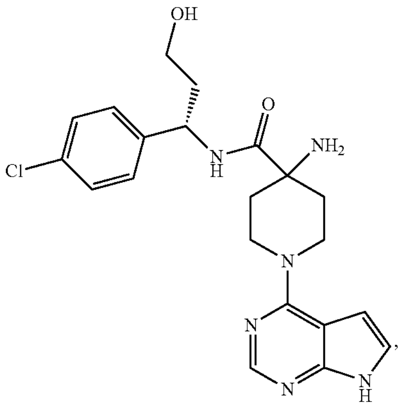

or a pharmaceutically acceptable salt thereof.

The compound of Formula (I) is also known by the International Nonproprietary Name of acalabrutinib. International Application WO2013/010868 discloses acalabrutinib (Example 6) and describes the synthesis of acalabrutinib. The synthesis of acalabrutinib is further described in International Application No. PCT/EP2019/072991 filed Aug. 28, 2019. International Application WO2013/010868 and International Application No. PCT/EP2019/072991 are each incorporated by reference in their entirety.

The compound of Formula (II) is also known by the International Nonproprietary Name of capivasertib. WO2009/047563, which is incorporated by reference in its entirety, discloses capivasertib (Example 9) and describes the synthesis of capivasertib.

In another embodiment, the present disclosure relates to methods of treating a B-cell malignancy in a subject in need thereof, comprising administering to the subject a first amount of a compound of Formula I:

(I)

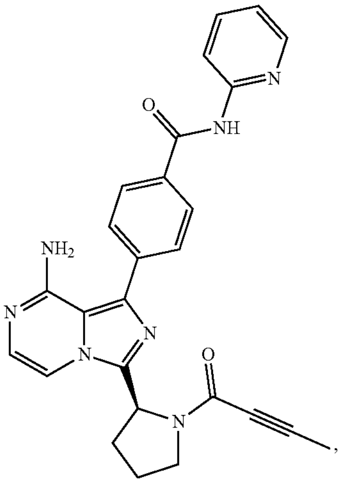

or a pharmaceutically acceptable salt thereof, and a second amount of a compound of Formula II:

(II)

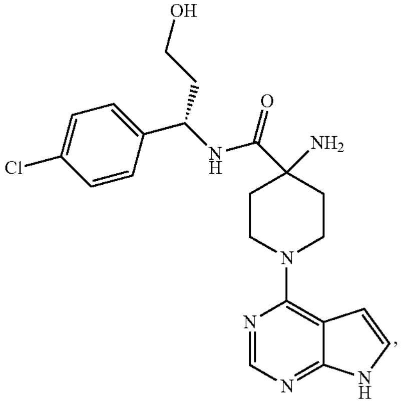

or a pharmaceutically acceptable salt thereof, wherein the first amount and the second amount together comprise a therapeutically effective amount. In another aspect, the first amount and the second amount together comprise a synergistic amount for treating the B-cell malignancy.

In some embodiments, the subject is a mammal. In one aspect, the subject is a companion animal. In another aspect, the subject is a canine, feline, or equine. In a preferred aspect, the subject is a human.

In some embodiments, acalabrutinib and/or capivasertib are administered in their non-salt forms (i.e., free base forms). In other embodiments, acalabrutinib and/or capivasertib are administered in their pharmaceutically acceptable salt forms. In still other embodiments, one of acalabrutinib and capivasertib is administered in non-salt form and the other of acalabrutinib and capivasertib is administered in pharmaceutically acceptable salt form.

In another embodiment, the present disclosure relates to use of a combination comprising a compound of Formula I:

(I)

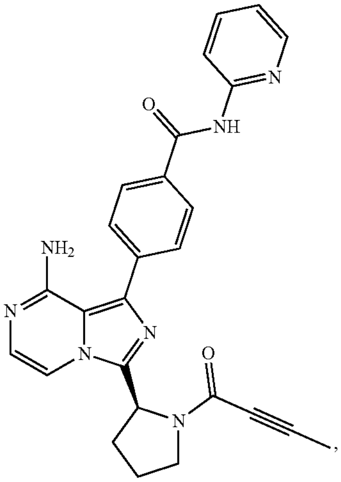

, or a pharmaceutically acceptable salt thereof, and a compound of Formula II:

(II)

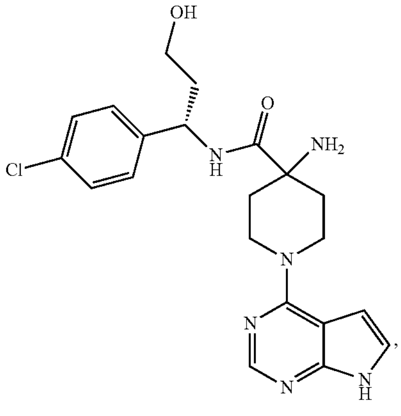

, or a pharmaceutically acceptable salt thereof, for the treatment of a B-cell malignancy.

In another embodiment, the present disclosure relates to use of a combination comprising a compound of Formula I:

(I)

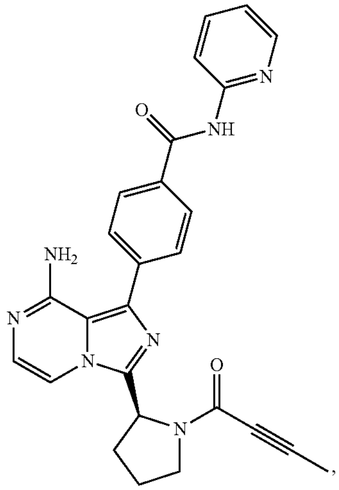

, or a pharmaceutically acceptable salt thereof, and a compound of Formula II:

(II)

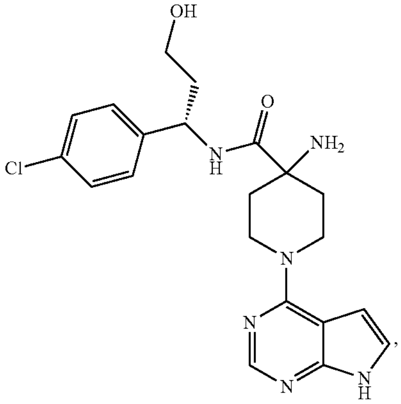

, or a pharmaceutically acceptable salt thereof, in the manufacture of a medicament for the treatment of a B-cell malignancy.

In some embodiments, the B-cell malignancy is aggressive lymphoma.

In some embodiments, the B-cell malignancy is non-Hodgkin lymphoma.

In some embodiments, the B-cell malignancy is selected from the group consisting of B-cell acute lymphoblastic leukemia, mature B-cell acute lymphoblastic leukemia, and diffuse large B-cell lymphoma.

In some embodiments, the B-cell malignancy is selected from the group consisting of mantle cell lymphoma; follicular lymphoma; de novo diffuse large B-cell lymphoma; transformed diffuse large B-cell lymphoma; T-cell/histiocyte-rich large B-cell lymphoma; primary cutaneous diffuse large B-cell lymphoma; leg-type primary cutaneous diffuse large B-cell lymphoma; Epstein-Barr virus-positive diffuse large B-cell lymphoma; diffuse large B-cell lymphoma associated with chronic inflammation; primary mediastinal large B-cell lymphoma; intravascular large B-cell lymphoma;

anaplastic lymphoma kinase-positive (ALK+) large B-cell lymphoma; and high-grade B-cell lymphoma with rearrangements of MYC and BCL2 or of BCL6 and MYC.

In some embodiments, the B-cell malignancy is selected from the group consisting of de novo diffuse large B-cell lymphoma; transformed diffuse large B-cell lymphoma; T-cell/histiocyte-rich large B-cell lymphoma; primary cutaneous diffuse large B-cell lymphoma; leg-type primary cutaneous diffuse large B-cell lymphoma; Epstein-Barr virus-positive diffuse large B-cell lymphoma; diffuse large B-cell lymphoma associated with chronic inflammation; primary mediastinal large B-cell lymphoma; intravascular large B-cell lymphoma; anaplastic lymphoma kinase-positive (ALK+) large B-cell lymphoma; and high-grade B-cell lymphoma with rearrangements of MYC and BCL2 or of BCL6 and MYC.

In some embodiments, the B-cell malignancy is diffuse large B-cell lymphoma. In one aspect, the diffuse large B-cell lymphoma is selected from the group consisting of de novo diffuse large B-cell lymphoma, relapsed/refractory diffuse large B-cell lymphoma, and transformed diffuse large B-cell lymphoma.

In some embodiments, the diffuse large B-cell lymphoma is de novo diffuse large B-cell lymphoma.

In some embodiments, the diffuse large B-cell lymphoma is relapsed/refractory diffuse large B-cell lymphoma.

In some embodiments, the diffuse large B-cell lymphoma is transformed diffuse large B-cell lymphoma. In one aspect, the transformed diffuse large B-cell lymphoma is Richter syndrome.

In some embodiments, the diffuse large B-cell lymphoma is selected from the group consisting of the germinal center B-cell diffuse large B-cell lymphoma and activated B-cell diffuse large B-cell lymphoma subtypes. In one aspect, the diffuse large B-cell lymphoma is selected from the group consisting of relapsed/refractory germinal center B-cell diffuse large B-cell lymphoma and relapsed/refractory activated B-cell diffuse large B-cell lymphoma.

In some embodiments, the diffuse large B-cell lymphoma is activated B-cell diffuse large B-cell lymphoma. In one aspect, the diffuse large B-cell lymphoma is relapsed/refractory activated B-cell diffuse large B-cell lymphoma.

Diagnosis of the specific B-cell malignancy from which a subject is suffering can be made in accordance with accepted clinical practice. See, for example, the 2016 classification guidelines established by the World Health Organization (WHO) for lymphoid neoplasms, or the National Comprehensive Cancer Network (NCCN) classification guidelines for non-Hodgkin lymphoma.

In some embodiments, the human subject has previously received at least one prior chemo-immunotherapy for the B-cell malignancy. In one aspect, the B-cell malignancy is diffuse large B-cell lymphoma. In another aspect, the prior chemo-immunotherapy comprises treatment with rituximab, cyclophosphamide, doxorubicin, vincristine, and prednisone (i.e., R-CHOP).

III. Combination Dosages and Dosing Regimens

The amount of acalabrutinib and capivasertib administered to the subject will be dependent on the subject being treated, the severity of the disorder or condition, the rate of administration, the disposition of the compounds, and the discretion of the prescribing physician. In the various embodiments described below and throughout this specification and unless otherwise specifically stated, "acalabrutinib" refers to acalabrutinib free base or a pharmaceutically acceptable salt thereof; "capivasertib" refers to capivasertib free base or a pharmaceutically acceptable salt thereof; and the amount of acalabrutinib or capivasertib per dose recited is based upon the amount of acalabrutinib free base or capivasertib free base, respectively.

An effective amount of the combination of acalabrutinib and capivasertib can be administered simultaneously, separately, or sequentially, and in either single or multiple doses, by any of the accepted modes of administration of agents having similar utilities, including rectal, buccal, intranasal and transdermal routes, by intra-arterial injection, intravenously, parenterally, intramuscularly, subcutaneously, orally, topically, or as an inhalant. In preferred embodiments, both acalabrutinib and capivasertib are administered orally to a human subject.

In some embodiments, acalabrutinib and capivasertib are administered simultaneously to the subject.

In some embodiments, acalabrutinib and capivasertib are administered separately to the subject.

In some embodiments, acalabrutinib and capivasertib are administered sequentially to the subject.

In some embodiments, acalabrutinib is administered before capivasertib is administered within a dosing cycle. In one aspect, acalabrutinib is administered at least 2 hours, at least 4 hours, at least 6 hours, at least 8 hours, at least 12 hours, at least 16 hours, at least 24 hours, or at least 48 hours before capivasertib is administered within a dosing cycle. In another aspect, acalabrutinib is administered no more than 2 hours, no more than 4 hours, no more than 6 hours, no more than 8 hours, no more than 12 hours, no more than 16 hours, no more than 24 hours, or no more than 48 hours before capivasertib is administered within a dosing cycle. In another aspect, acalabrutinib is administered from 2 to 4 hours before; from 4 to 6 hours before; from 6 to 8 hours before; from 8 to 12 hours before; from 12 to 16 hours before; from 16 to 24 hours before; from 20 to 28 hours before; or from 24 to 48 hours before capivasertib is administered within a dosing cycle.

In some embodiments, capivasertib is administered before acalabrutinib is administered within a dosing cycle. In one aspect, capivasertib is administered at least 2 hours, at least 4 hours, at least 6 hours, at least 8 hours, at least 12 hours, at least 16 hours, at least 24 hours, or at least 48 hours before acalabrutinib is administered within a dosing cycle. In another aspect, capivasertib is administered no more than 2 hours, no more than 4 hours, no more than 6 hours, no more than 8 hours, no more than 12 hours, no more than 16 hours, no more than 24 hours, or no more than 48 hours before acalabrutinib is administered within a dosing cycle. In another aspect, capivasertib is administered from 2 to 4 hours before; from 4 to 6 hours before; from 6 to 8 hours before; from 8 to 12 hours before; from 12 to 16 hours before; from 16 to 24 hours before; from 20 to 28 hours before; or from 24 to 48 hours before acalabrutinib is administered within a dosing cycle.

A. Acalabrutinib Dosages and Dosing Regimens

In combinations with capivasertib, acalabrutinib generally is administered at a daily dosage from about 50 mg to about 400 mg. In some embodiments, acalabrutinib is administered at a daily dosage from about 50 mg to about 350 mg. In one aspect, acalabrutinib is administered at a daily dosage from about 50 mg to about 300 mg. In another aspect, acalabrutinib is administered at a daily dosage from about 50 mg to about 250 mg. In another aspect, acalabrutinib is administered at a daily dosage from about 75 mg to about 225 mg. In another aspect, acalabrutinib is administered at a daily dosage from about 100 mg to about 200 mg. In another aspect, acalabrutinib is administered at a daily dosage from about 75 mg to about 125 mg. In another aspect, acalabrutinib is administered at a daily dosage from about 175 mg to about 225 mg. In another aspect, acalabrutinib is administered at a daily dosage of about 100 mg. In another aspect, acalabrutinib is administered at a daily dosage of about 200 mg. In another aspect, acalabrutinib is administered at a daily dosage of about 400 mg.

In some embodiments, acalabrutinib is administered to the subject once daily (QD). In one aspect, acalabrutinib is administered at a dosage from about 50 mg to about 400 mg once daily. In another aspect, acalabrutinib is administered at a dosage from about 50 mg to about 350 mg once daily. In another aspect, acalabrutinib is administered at a dosage from about 50 mg to about 300 mg once daily. In another aspect, acalabrutinib is administered at a dosage from about 50 mg to about 250 mg once daily. In another aspect, acalabrutinib is administered at a dosage from about 75 mg to about 225 mg once daily. In another aspect, acalabrutinib is administered at a dosage from about 100 mg to about 200 mg once daily. In another aspect, acalabrutinib is administered at a dosage from about 75 mg to about 125 mg once daily. In another aspect, acalabrutinib is administered at a dosage from about 175 mg to about 225 mg once daily. In another aspect, acalabrutinib is administered at a dosage of about 100 mg once daily. In another aspect, acalabrutinib is administered at a dosage of about 200 mg once daily. In another aspect, acalabrutinib is initially administered at a dosage of about 200 mg once daily and the acalabrutinib dosage is subsequently reduced during the dosing cycle to a dosage of about 100 mg once daily.

In some embodiments, acalabrutinib is administered to the subject twice daily (BID). In one aspect, acalabrutinib is administered at a dosage from about 25 mg to about 200 mg twice daily. In another aspect, acalabrutinib is administered at a dosage from about 25 mg to about 150 mg twice daily. In another aspect, acalabrutinib is administered at a dosage from about 50 mg to about 125 mg twice daily. In another aspect, acalabrutinib is administered at a dosage from about 90 mg to about 110 mg twice daily. In another aspect, acalabrutinib is administered at a dosage from about 95 mg to about 105 mg twice daily. In another aspect, acalabrutinib is administered at a dosage of about 100 mg twice daily. In another aspect, acalabrutinib is initially administered at a dosage of about 100 mg twice daily and the acalabrutinib dosage is subsequently reduced during the dosing cycle to a dosage of about 100 mg once daily. In another aspect, acalabrutinib is administered at a dosage of about 200 mg twice daily.

In some embodiments, acalabrutinib is administered under a continuous dosing schedule. A continuous dosing schedule includes no holidays during a dosing cycle. For example, in a seven-day dosing cycle, continuously dosed acalabrutinib would be given on days one, two, three, four, five, six, and seven. The dosing cycle would then repeat for the desired number of cycles. In one aspect, for example, acalabrutinib is administered for more than 1, 2, 3, 4, 5, 6, 7, 14, 21, 28, 35, 42, 49, or 56 days. In one aspect, the dosing cycle is 28 days. Administration of acalabrutinib and repeat of the dosing cycle can continue as long as tolerable and beneficial for the subject.

In some embodiments, acalabrutinib is administered to the subject under an intermittent dosing schedule. In contrast to a continuous dosing schedule, an intermittent dosage schedule can include dosage holidays. For example, intermittently dosed acalabrutinib in a seven-day dosing cycle might be given on days one and two, but not given on days three, four, five, six, or seven. The dosing cycle would then repeat. This illustration could be referred to as a 2 days on/5 days off schedule, where acalabrutinib is given for two days followed by a five-day holiday. Similarly, intermittently dosed acalabrutinib in a seven-day dosing cycle might be given on days one, two, three, and four, but not given on days five, six, or seven. The dosing cycle would then repeat. This illustration could be referred to as a 4 days on/3 days off schedule, where acalabrutinib is given for four days followed by a three-day holiday.

B. Capivasertib Dosages and Dosing Regimens

In combinations with acalabrutinib, capivasertib generally is administered to the subject at a daily dosage from about 100 mg to about 1600 mg. In some embodiments, capivasertib is administered at a daily dosage from about 150 mg to about 1500 mg. In one aspect, capivasertib is administered at a daily dosage from about 200 mg to about 1400 mg. In another aspect, capivasertib is administered at a daily dosage from about 300 mg to about 1300 mg. In another aspect, capivasertib is administered at a daily dosage from about 400 mg to about 1200 mg. In another aspect, capivasertib is administered at a daily dosage from about 500 mg to about 1100 mg. In another aspect, capivasertib is administered at a daily dosage from about 600 mg to about 1000 mg.

In some embodiments, capivasertib is administered to the subject once daily (QD). In one aspect, capivasertib is administered at a dosage from about 100 mg to about 1000 mg once daily. In another aspect, capivasertib is administered at a dosage from about 150 mg to about 900 mg once daily. In another aspect, capivasertib is administered at a dosage from about 200 mg to about 850 mg once daily. In another aspect, capivasertib is administered at a dosage from about 250 mg to about 800 mg once daily. In another aspect, capivasertib is administered at a dosage from about 300 mg to about 750 mg once daily. In another aspect, capivasertib is administered at a dosage from about 350 mg to about 700 mg once daily. In another aspect, capivasertib is administered at a dosage from about 400 mg to about 650 mg once daily.

In some embodiments, capivasertib is administered to the subject twice daily (BID). In one aspect, capivasertib is administered at a dosage from about 50 mg to about 900 mg twice daily. In another aspect, capivasertib is administered at a dosage from about 100 mg to about 875 mg twice daily. In another aspect, capivasertib is administered at a dosage from about 200 mg to about 850 mg twice daily. In another aspect, capivasertib is administered at a dosage from about 250 mg to about 825 mg twice daily. In another aspect, capivasertib is administered at a dosage from about 150 mg to about 250 mg twice daily. In another aspect, capivasertib is administered at a dosage from about 250 mg to about 350 mg twice daily. In another aspect, capivasertib is administered at a dosage from about 350 mg to about 450 mg twice daily. In another aspect, capivasertib is administered at a dosage from about 450 mg to about 550 mg twice daily. In another aspect, capivasertib is administered at a dosage from about 550 mg to about 650 mg twice daily. In another aspect, capivasertib is administered at a dosage from about 650 mg to about 750 mg twice daily. In another aspect, capivasertib is administered at a dosage from about 750 mg to about 850 mg twice daily. In another aspect, capivasertib is administered at a dosage of about 160 mg twice daily. In another aspect, capivasertib is administered at a dosage of about 200 mg twice daily. In another aspect, capivasertib is administered at a dosage of about 240 mg twice daily. In another aspect, capivasertib is administered at a dosage of about 280 mg twice daily. In another aspect, capivasertib is administered at a dosage of about 320 mg twice daily. In another aspect, capivasertib is administered at a dosage of about 360 mg twice daily. In another aspect, capivasertib is administered at a dosage of about 400 mg twice daily. In another aspect, capivasertib is administered at a dosage of about 440 mg twice daily. In another aspect, capivasertib is administered at a dosage of about 480 mg twice daily. In another aspect, capivasertib is administered at a dosage of about 520 mg twice daily. In another aspect, capivasertib is administered at a dosage of about 560 mg twice daily. In another aspect, capivasertib is administered at a dosage of about 600 mg twice daily. In another aspect, capivasertib is administered at a dosage of about 640 mg twice daily. In another aspect, capivasertib is administered at a dosage of about 680 mg twice daily. In another aspect, capivasertib is administered at a dosage of about 720 mg twice daily. In another aspect, capivasertib is administered at a dosage of about 760 mg twice daily. In another aspect, capivasertib is administered at a dosage of about 800 mg twice daily.

In some embodiments, capivasertib is administered under a continuous dosing schedule. In one aspect, for example, capivasertib is administered for more than 1, 2, 3, 4, 5, 6, 7, 14, 21, 28, 35, 42, 49, or 56 days. In another aspect, the dosing cycle is 28 days. Administration of capivasertib and repeat of the dosing cycle can continue as long as tolerable and beneficial for the subject.

In some embodiments, capivasertib is administered once daily (QD) under a continuous dosing schedule. In one aspect, capivasertib is administered once daily under a continuous dosing schedule at a dosage from about 100 mg to about 900 mg. In another aspect, capivasertib is administered once daily under a continuous dosing schedule at a dosage from about 150 mg to about 875 mg. In another aspect, capivasertib is administered once daily under a continuous dosing schedule at a dosage from about 175 mg to about 850 mg. In another aspect, capivasertib is administered once daily under a continuous dosing schedule at a dosage from about 200 mg to about 825 mg. In another aspect, capivasertib is administered once daily under a continuous dosing schedule at a dosage from about 225 mg to about 800 mg. In another aspect, capivasertib is administered once daily under a continuous dosing schedule at a dosage from about 250 mg to about 750 mg. In another aspect, capivasertib is administered once daily under a continuous dosing schedule at a dosage from about 275 mg to about 700 mg. In another aspect, capivasertib is administered once daily under a continuous dosing schedule at a dosage from about 300 mg to about 650 mg.

In some embodiments, capivasertib is administered twice daily (BID) under a continuous dosing schedule. In one aspect, capivasertib is administered under a continuous dosing schedule at a dosage from about 100 mg to about 800 mg twice daily. In another aspect, capivasertib is administered under a continuous dosing schedule at a dosage from about 150 mg to about 750 mg twice daily. In another aspect, capivasertib is administered under a continuous dosing schedule at a dosage from about 200 mg to about 700 mg twice daily. In another aspect, capivasertib is administered under a continuous dosing schedule at a dosage from about 225 mg to about 650 mg twice daily. In another aspect, capivasertib is administered under a continuous dosing schedule at a dosage from about 250 mg to about 650 mg twice daily. In another aspect, capivasertib is administered under a continuous dosing schedule at a dosage from about 300 mg to about 600 mg twice daily. In another aspect, capivasertib is administered under a continuous dosing schedule at a dosage from about 200 mg to about 300 mg twice daily. In another aspect, capivasertib is administered under a continuous dosing schedule at a dosage from about 300 mg to about 400 mg twice daily. In another aspect, capivasertib is administered under a continuous dosing schedule at a dosage from about 400 mg to about 500 mg twice daily. In another aspect, capivasertib is administered under a continuous dosing schedule at a dosage from about 500 mg to about 600 mg twice daily. In another aspect, capivasertib is administered under a continuous dosing schedule at a dosage from about 600 mg to about 700 mg twice daily. In another aspect, capivasertib is administered under a continuous dosing schedule at a dosage from about 700 mg to about 800 mg twice daily. In another aspect, capivasertib is administered under a continuous dosing schedule at a dosage of about 160 mg twice daily. In another aspect, capivasertib is administered under a continuous dosing schedule at a dosage of about 200 mg twice daily. In another aspect, capivasertib is administered under a continuous dosing schedule at a dosage of about 240 mg twice daily. In another aspect, capivasertib is administered under a continuous dosing schedule at a dosage of about 280 mg twice daily. In another aspect, capivasertib is administered under a continuous dosing schedule at a dosage of about 320 mg twice daily. In another aspect, capivasertib is administered under a continuous dosing schedule at a dosage of about 360 mg twice daily. In another aspect, capivasertib is administered under a continuous dosing schedule at a dosage of about 400 mg twice daily. In another aspect, capivasertib is administered under a continuous dosing schedule at a dosage of about 440 mg twice daily. In another aspect, capivasertib is administered under a continuous dosing schedule at a dosage of about 480 mg twice daily. In another aspect, capivasertib is administered under a continuous dosing schedule at a dosage of about 520 mg twice daily. In another aspect, capivasertib is administered under a continuous dosing schedule at a dosage of about 580 mg twice daily. In another aspect, capivasertib is administered under a continuous dosing schedule at a dosage of about 600 mg twice daily. In another aspect, capivasertib is administered under a continuous dosing schedule at a dosage of about 640 mg twice daily. In another aspect, capivasertib is administered under a continuous dosing schedule at a dosage of about 680 mg twice daily. In another aspect, capivasertib is administered under a continuous dosing schedule at a dosage of about 720 mg twice daily. In another aspect, capivasertib is administered under a continuous dosing schedule at a dosage of about 760 mg twice daily. In another aspect, capivasertib is administered under a continuous dosing schedule at a dosage of about 800 mg twice daily.

In some embodiments, capivasertib is administered to the subject on an intermittent dosage schedule. Administering capivasertib on an intermittent dosage schedule can, for example, have greater effectiveness and/or tolerability than on a continuous dosing schedule. In one aspect, capivasertib is intermittently dosed on a 1 day on/6 days off schedule (i.e., capivasertib is administered for one day followed by a six-day holiday). In another aspect, capivasertib is intermittently dosed on a 2 days on/5 days off schedule (i.e., capivasertib is administered for two days followed by a five-day holiday). In another aspect, capivasertib is intermittently dosed on a 3 days on/4 days off schedule (i.e., capivasertib is administered for three days followed by a four-day holiday). In another aspect, capivasertib is intermittently dosed on a 4 days on/3 days off schedule (i.e., capivasertib is administered for four days followed by a three-day holiday). In another aspect, capivasertib is intermittently dosed on a 5 days on/2 days off schedule (i.e., capivasertib is administered for five days followed by a two-day holiday). In another aspect, capivasertib is intermittently dosed on a 6 days on/1 day off schedule (i.e., capivasertib is administered for six days followed by a one-day holiday).

The dosing cycle of such embodiments would then repeat as long as tolerable and beneficial for the subject. In some embodiments, the dosing cycle is 7 days. In one aspect, the dosing cycle is 14 days. In another aspect, the dosing cycle is 21 days. In another aspect, the dosing cycle is 28 days. In another aspect, the dosing cycle is two months. In another aspect, the dosing cycle is six months. In another aspect, the dosing cycle is one year.

In some embodiments, the dosing cycle is 28 days, but capivasertib is not co-administered to the subject during the fourth week of the dosing cycle (i.e., there is a capivasertib drug holiday during the final week of the dosing cycle).

In some embodiments, capivasertib is administered once daily (QD) under an intermittent dosing schedule. In one aspect, capivasertib is administered once daily under an intermittent dosing schedule at a dosage from about 100 mg to about 900 mg. In another aspect, capivasertib is administered once daily under an intermittent dosing schedule at a dosage from about 150 mg to about 850 mg. In another aspect, capivasertib is administered once daily under an intermittent dosing schedule at a dosage from about 175 mg to about 800 mg. In another aspect, capivasertib is administered once daily under an intermittent dosing schedule at a dosage from about 200 mg to about 750 mg. In another aspect, capivasertib is administered once daily under an intermittent dosing schedule at a dosage from about 225 mg to about 725 mg. In another aspect, capivasertib is administered once daily under an intermittent dosing schedule at a dosage from about 250 mg to about 700 mg. In another aspect, capivasertib is administered once daily under an intermittent dosing schedule at a dosage from about 275 mg to about 675 mg. In another aspect, capivasertib is administered once daily under an intermittent dosing schedule at a dosage from about 300 mg to about 650 mg.

In some embodiments, capivasertib is administered twice daily (BID) under an intermittent dosing schedule. In one aspect, capivasertib is administered under an intermittent dosing schedule at a dosage from about 100 mg to about 800 mg twice daily. In another aspect, capivasertib is administered under an intermittent dosing schedule at a dosage from about 150 mg to about 750 mg twice daily. In another aspect, capivasertib is administered under an intermittent dosing schedule at a dosage from about 200 mg to about 700 mg twice daily. In another aspect, capivasertib is administered under an intermittent dosing schedule at a dosage from about 225 mg to about 675 mg twice daily. In another aspect, capivasertib is administered under an intermittent dosing schedule at a dosage from about 250 mg to about 650 mg twice daily. In another aspect, capivasertib is administered under an intermittent dosing schedule at a dosage from about 300 mg to about 625 mg twice daily. In another aspect, capivasertib is administered under an intermittent dosing schedule at a dosage from about 200 mg to about 300 mg twice daily. In another aspect, capivasertib is administered under an intermittent dosing schedule at a dosage from about 300 mg to about 400 mg twice daily. In another aspect, capivasertib is administered under an intermittent dosing schedule at a dosage from about 400 mg to about 500 mg twice daily. In another aspect, capivasertib is administered under an intermittent dosing schedule at a dosage from about 500 mg to about 600 mg twice daily. In another aspect, capivasertib is administered under an intermittent dosing schedule at a dosage from about 600 mg to about 700 mg twice daily. In another aspect, capivasertib is administered under an intermittent dosing schedule at a dosage from about 700 mg to about 800 mg twice daily. In another aspect, capivasertib is administered under an intermittent dosing schedule at a dosage of about 160 mg twice daily. In another aspect, capivasertib is administered under an intermittent dosing schedule at a dosage of about 200 mg twice daily. In another aspect, capivasertib is administered under an intermittent dosing schedule at a dosage of about 240 mg twice daily. In another aspect, capivasertib is administered under an intermittent dosing schedule at a dosage of about 280 mg twice daily. In another aspect, capivasertib is administered under an intermittent dosing schedule at a dosage of about 320 mg twice daily. In another aspect, capivasertib is administered under an intermittent dosing schedule at a dosage of about 360 mg twice daily. In another aspect, capivasertib is administered under an intermittent dosing schedule at a dosage of about 400 mg twice daily. In another aspect, capivasertib is administered under an intermittent dosing schedule at a dosage of about 440 mg twice daily. In another aspect, capivasertib is administered under an intermittent dosing schedule at a dosage of about 480 mg twice daily. In another aspect, capivasertib is administered under an intermittent dosing schedule at a dosage of about 520 mg twice daily. In another aspect, capivasertib is administered under an intermittent dosing schedule at a dosage of about 580 mg twice daily. In another aspect, capivasertib is administered under an intermittent dosing schedule at a dosage of about 600 mg twice daily. In another aspect, capivasertib is administered under an intermittent dosing schedule at a dosage of about 640 mg twice daily. In another aspect, capivasertib is administered under an intermittent dosing schedule at a dosage of about 680 mg twice daily. In another aspect, capivasertib is administered under an intermittent dosing schedule at a dosage of about 720 mg twice daily. In another aspect, capivasertib is administered under an intermittent dosing schedule at a dosage of about 760 mg twice daily. In another aspect, capivasertib is administered under an intermittent dosing schedule at a dosage of about 800 mg twice daily.

C. Illustrative Examples

In some embodiments, both acalabrutinib and capivasertib are dosed continuously in a dosing cycle. In one aspect, both acalabrutinib and capivasertib are orally dosed continuously in a dosing cycle. In another aspect, both acalabrutinib and capivasertib are orally dosed continuously in a dosing cycle, and the amount of acalabrutinib administered is from about 75 mg to about 125 mg twice daily. In another aspect, both acalabrutinib and capivasertib are orally dosed continuously in a dosing cycle, and the amount of acalabrutinib administered is about 100 mg twice daily. In another aspect, both acalabrutinib and capivasertib are orally dosed continuously in a dosing cycle, the amount of acalabrutinib initially administered at the beginning of the dosing cycle is about 100 mg twice daily, and the amount of acalabrutinib administered is subsequently reduced during the dosing cycle to a dosage of about 100 mg once daily.

In some embodiments, acalabrutinib is dosed continuously and capivasertib is dosed intermittently in a dosing cycle. In one aspect, acalabrutinib is orally dosed continuously and capivasertib is orally dosed intermittently in a dosing cycle. In another aspect, acalabrutinib is orally dosed continuously and capivasertib is orally dosed intermittently in a dosing cycle, and the amount of acalabrutinib administered is from about 75 mg to about 125 mg twice daily. In another aspect, acalabrutinib is orally dosed continuously and capivasertib is orally dosed intermittently in a dosing cycle, and the amount of acalabrutinib administered is about 100 mg twice daily. In another aspect, acalabrutinib is orally dosed continuously and capivasertib is orally dosed intermittently in a dosing cycle, the amount of acalabrutinib initially administered at the beginning of the dosing cycle is about 100 mg twice daily, and the amount of acalabrutinib administered is subsequently reduced during the dosing cycle to a dosage of about 100 mg once daily.

In some embodiments, acalabrutinib is dosed continuously and capivasertib is dosed intermittently on a 1 day on/6 days off schedule in a dosing cycle. In one aspect, acalabrutinib is orally dosed continuously in an amount of about 75 mg to about 125 mg twice daily and capivasertib is orally dosed intermittently on a 1 day on/6 days off schedule in a dosing cycle. In another aspect, acalabrutinib is orally dosed continuously in an amount of about 100 mg twice daily and capivasertib is orally dosed intermittently on a 1 day on/6 days off schedule in a dosing cycle. In another aspect, acalabrutinib is orally dosed continuously and capivasertib is orally dosed intermittently on a 1 day on/6 days off schedule in a dosing cycle, the amount of acalabrutinib initially administered at the beginning of the dosing cycle is about 100 mg twice daily, and the amount of acalabrutinib administered is subsequently reduced during the dosing cycle to a dosage of about 100 mg once daily.

In some embodiments, acalabrutinib is dosed continuously and capivasertib is dosed intermittently on a 2 days on/5 days off schedule in a dosing cycle. In one aspect, acalabrutinib is orally dosed continuously in an amount of about 75 mg to about 125 mg twice daily and capivasertib is orally dosed intermittently on a 2 days on/5 days off schedule in a dosing cycle. In another aspect, acalabrutinib is orally dosed continuously in an amount of about 100 mg twice daily and capivasertib is orally dosed intermittently on a 2 days on/5 days off schedule in a dosing cycle. In another aspect, acalabrutinib is orally dosed continuously and capivasertib is orally dosed intermittently on a 2 days on/5 days off schedule in a dosing cycle, the amount of acalabrutinib initially administered at the beginning of the dosing cycle is about 100 mg twice daily, and the amount of acalabrutinib administered is subsequently reduced during the dosing cycle to a dosage of about 100 mg once daily.

In some embodiments, acalabrutinib is dosed continuously and capivasertib is dosed intermittently on a 3 days on/4 days off schedule in a dosing cycle. In one aspect, acalabrutinib is orally dosed continuously in an amount of about 75 mg to about 125 mg twice daily and capivasertib is orally dosed intermittently on a 3 days on/4 days off schedule in a dosing cycle. In another aspect, acalabrutinib is orally dosed continuously in an amount of 100 mg twice daily and capivasertib is orally dosed intermittently on a 3 days on/4 days off schedule in a dosing cycle. In another aspect, acalabrutinib is orally dosed continuously and capivasertib is orally dosed intermittently on a 3 days on/4 days off schedule in a dosing cycle, the amount of acalabrutinib initially administered at the beginning of the dosing cycle is about 100 mg twice daily, and the amount of acalabrutinib administered is subsequently reduced during the dosing cycle to a dosage of about 100 mg once daily.

In some embodiments, acalabrutinib is dosed continuously and capivasertib is dosed intermittently on a 4 days on/3 days off schedule in a dosing cycle. In one aspect, acalabrutinib is orally dosed continuously in an amount of about 75 mg to about 125 mg twice daily and capivasertib is orally dosed intermittently on a 4 days on/3 days off schedule in a dosing cycle. In another aspect, acalabrutinib is orally dosed continuously in an amount of 100 mg twice daily and capivasertib is orally dosed intermittently on a 4 days on/3 days off schedule in a dosing cycle. In another aspect, acalabrutinib is orally dosed continuously and capivasertib is orally dosed intermittently on a 4 days on/3 days off schedule in a dosing cycle, the amount of acalabrutinib initially administered at the beginning of the dosing cycle is about 100 mg twice daily, and the amount of acalabrutinib administered is subsequently reduced during the dosing cycle to a dosage of about 100 mg once daily.

In some embodiments, acalabrutinib is dosed continuously and capivasertib is dosed intermittently on a 5 days on/2 days off schedule in a dosing cycle. In one aspect, acalabrutinib is orally dosed continuously in an amount of about 75 mg to about 125 mg twice daily and capivasertib is orally dosed intermittently on a 5 days on/2 days off schedule in a dosing cycle. In another aspect, acalabrutinib is orally dosed continuously in an amount of 100 mg twice daily and capivasertib is orally dosed intermittently on a 5 days on/2 days off schedule in a dosing cycle. In another aspect, acalabrutinib is orally dosed continuously and capivasertib is orally dosed intermittently on a 5 days on/2 days off schedule in a dosing cycle, the amount of acalabrutinib initially administered at the beginning of the dosing cycle is about 100 mg twice daily, and the amount of acalabrutinib administered is subsequently reduced during the dosing cycle to a dosage of about 100 mg once daily.

In some embodiments, acalabrutinib is dosed continuously and capivasertib is dosed intermittently on a 6 days on/1 day off schedule in a dosing cycle. In one aspect, acalabrutinib is orally dosed continuously in an amount of about 75 mg to about 125 mg twice daily and capivasertib is orally dosed intermittently on a 6 days on/1 day off schedule in a dosing cycle. In another aspect, acalabrutinib is orally dosed continuously in an amount of about 100 mg twice daily and capivasertib is orally dosed intermittently on a 6 days on/1 day off schedule in a dosing cycle. In another aspect, acalabrutinib is orally dosed continuously and capivasertib is orally dosed intermittently on a 6 days on/1 day off schedule in a dosing cycle, the amount of acalabrutinib initially administered at the beginning of the dosing cycle is about mg twice daily, and the amount of acalabrutinib administered is subsequently reduced during the dosing cycle to a dosage of about 100 mg once daily.

In some embodiments, both acalabrutinib and capivasertib are orally dosed continuously in a dosing cycle, the amount of acalabrutinib administered daily is about 75 mg to about 225 mg, and the amount of capivasertib administered daily is about 100 mg to about 1600 mg. In one aspect, both acalabrutinib and capivasertib are orally dosed continuously in a dosing cycle, acalabrutinib is administered once daily in an amount of about 75 mg to about 225 mg, and capivasertib is administered once daily in an amount about 100 mg to about 900 mg. In another aspect, both acalabrutinib and capivasertib are orally dosed continuously in a dosing cycle, acalabrutinib is administered in an amount of about 75 mg to about 125 mg twice daily, and capivasertib is administered in an amount of about 150 mg to about 850 mg twice daily. In another aspect, both acalabrutinib and capivasertib are orally dosed continuously in a dosing cycle, acalabrutinib is administered in an amount of about 100 mg twice daily, and capivasertib is administered in an amount of about 200 mg to about 800 mg twice daily. In another aspect, both acalabrutinib and capivasertib are orally dosed continuously in a dosing cycle, acalabrutinib is initially administered at the beginning of the dosing cycle in an amount of about 100 mg twice daily, capivasertib is administered in an amount of about 200 mg to about 800 mg twice daily, and the amount of acalabrutinib administered is subsequently reduced during the dosing cycle to an amount of about 100 mg once daily.

In some embodiments, acalabrutinib is dosed continuously and capivasertib is dosed intermittently in a dosing cycle, the amount of acalabrutinib administered daily is about 75 mg to about 225 mg, and the amount of capivasertib administered is about 100 mg to about 1600 mg on each day of administration. In one aspect, acalabrutinib is dosed continuously and capivasertib is dosed intermittently in a dosing cycle, acalabrutinib is administered once daily in an amount of about 75 mg to about 225 mg, and capivasertib is administered once daily in an amount about 100 mg to about 900 mg on each day of administration. In another aspect, acalabrutinib is dosed continuously and capivasertib is dosed intermittently in a dosing cycle, acalabrutinib is administered in an amount of about 75 mg to about 125 mg twice daily, and capivasertib is administered in an amount of about 150 mg to about 850 mg twice daily on each day of administration. In another aspect, acalabrutinib is dosed continuously and capivasertib is dosed intermittently in a dosing cycle, acalabrutinib is administered in an amount of about 100 mg twice daily, and capivasertib is administered in an amount of about 200 mg to about 800 mg twice daily on each day of administration. In another aspect, acalabrutinib is dosed continuously and capivasertib is dosed intermittently in a dosing cycle, acalabrutinib is initially administered at the beginning of the dosing cycle in an amount of about 100 mg twice daily, capivasertib is administered in an amount of about 200 mg to about 800 mg twice daily on each day of administration, and the amount of acalabrutinib administered is subsequently reduced during the dosing cycle to an amount of about 100 mg once daily.

In some embodiments, acalabrutinib is dosed continuously and capivasertib is dosed intermittently on a 2 days on/5 days off schedule in a dosing cycle, the amount of acalabrutinib administered daily is about 75 mg to about 225 mg, and the amount of capivasertib administered is about 100 mg to about 1600 mg on each day of administration. In one aspect, acalabrutinib is orally dosed continuously and capivasertib is orally dosed intermittently on a 2 days on/5 days off schedule in a dosing cycle, acalabrutinib is administered once daily in an amount of about 75 mg to about 225 mg, and capivasertib is administered once daily in an amount about 100 mg to about 900 mg on each day of administration. In another aspect, acalabrutinib is orally dosed continuously and capivasertib is orally dosed intermittently on a 2 days on/5 days off schedule in a dosing cycle, acalabrutinib is administered in an amount of about 75 mg to about 125 mg twice daily, and capivasertib is administered in an amount of about 150 mg to about 850 mg twice daily on each day of administration.

In some embodiments, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 200 mg to about 800 mg twice daily on each day of administration. In one aspect, acalabrutinib is orally dosed continuously and capivasertib is orally dosed intermittently on a 2 days on/5 days off schedule in a dosing cycle, acalabrutinib is initially administered at the beginning of the dosing cycle in an amount of about 100 mg twice daily, capivasertib is administered in an amount of about 200 mg to about 800 mg twice daily on each day of administration, and the amount of acalabrutinib administered is subsequently reduced during the dosing cycle to an amount of about 100 mg once daily. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 250 mg to about 350 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 350 mg to about 450 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 450 mg to about 550 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 550 mg to about 650 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 650 mg to about 750 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 750 mg to about 850 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 320 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 400 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 480 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 560 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 640 mg twice daily on each day of administration. In another aspect, acalabrutinib is orally dosed continuously and capivasertib is orally dosed intermittently on a 2 days on/5 days off schedule in a dosing cycle, acalabrutinib is administered in an amount of about 100 mg twice daily, and capivasertib is administered in an amount of about 800 mg twice daily on each day of administration.

In some embodiments, acalabrutinib is dosed continuously and capivasertib is dosed intermittently on a 4 days on/3 days off schedule in a dosing cycle, the amount of acalabrutinib administered daily is about 75 mg to about 225 mg, and the amount of capivasertib administered is about 100 mg to about 1600 mg on each day of administration. In one aspect, acalabrutinib is orally dosed continuously and capivasertib is orally dosed intermittently on a 4 days on/3 days off schedule in a dosing cycle, acalabrutinib is administered once daily in an amount of about 75 mg to about 225 mg, and capivasertib is administered once daily in an amount about 100 mg to about 900 mg on each day of administration. In another aspect, acalabrutinib is orally dosed continuously and capivasertib is orally dosed intermittently on a 4 days on/3 days off schedule in a dosing cycle, acalabrutinib is administered in an amount of about 75 mg to about 125 mg twice daily, and capivasertib is administered in an amount of about 150 mg to about 850 mg twice daily on each day of administration.

In some embodiments, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about of about 200 mg to about 800 mg twice daily on each day of administration. In one aspect, acalabrutinib is orally dosed continuously and capivasertib is orally dosed intermittently on a 4 days on/3 days off schedule in a dosing cycle, acalabrutinib is administered in an amount of about 100 mg twice daily, capivasertib is administered in an amount of about of about 200 mg to about 750 mg twice daily on each day of administration, and the amount of acalabrutinib administered is subsequently reduced during the dosing cycle to an amount of about 100 mg once daily. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 200 mg to about 700 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 250 mg to about 350 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 350 mg to about 450 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 450 mg to about 550 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 550 mg to about 650 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 650 mg to about 750 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 200 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 280 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 320 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 360 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 400 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 480 mg twice daily on each day of administration. In another aspect, acalabrutinib is orally dosed continuously and capivasertib is orally dosed intermittently on a 4 days on/3 days off schedule in a dosing cycle, acalabrutinib is administered in an amount of about 100 mg twice daily, and capivasertib is administered in an amount of about 640 mg twice daily on each day of administration.

IV. Pharmaceutical Compositions

The present disclosure further relates, in part, to pharmaceutical compositions comprising acalabrutinib, capivasertib, and a pharmaceutically acceptable carrier.

In some embodiments, the pharmaceutical composition comprises:

a compound of Formula I:

(I)

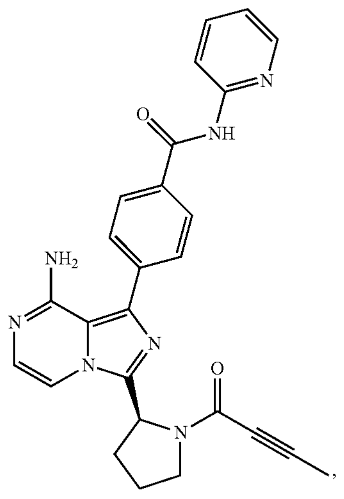

or a pharmaceutically acceptable salt thereof;

a compound of Formula II:

(II)

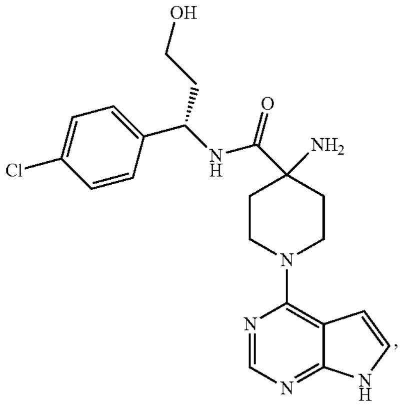

or a pharmaceutically acceptable salt thereof; and a pharmaceutically acceptable carrier.

In one aspect, the combination comprises acalabrutinib and capivasertib in their free base forms. In another aspect, the combination comprises acalabrutinib and capivasertib in their pharmaceutically acceptable salt forms. In another aspect, the combination comprises one of acalabrutinib and capivasertib in free base form and the other of acalabrutinib and capivasertib in pharmaceutically acceptable salt form.

The pharmaceutical compositions typically are formulated to provide a therapeutically effective amount of the combinations described in this specification. The pharmaceutical compositions also may comprise one or more pharmaceutically acceptable excipients, carriers, diluents, and/or fillers. Each of acalabrutinib and capivasertib as active ingredients can be combined in an intimate admixture with a pharmaceutical carrier according to conventional pharmaceutical compounding techniques. The carrier can take a wide variety of forms depending on the form of preparation desired for administration.

In some embodiments, the pharmaceutical compositions are suitable for oral administration. Pharmaceutical compositions suitable for oral administration can be presented as unit dosage forms, such as tablets, capsules, liquids, or aerosol sprays each containing a predetermined amount of the active ingredients. In one aspect, the pharmaceutical composition is an oral unit dosage form. In another aspect, the pharmaceutical composition is a tablet. In another aspect, the pharmaceutical composition is a capsule. In another aspect, the pharmaceutical composition is a liquid pharmaceutical composition suitable for oral consumption.

In some embodiments, the pharmaceutical composition is an oral unit dosage form comprising acalabrutinib, or a pharmaceutically acceptable salt thereof, in an amount from about 75 mg to about 125 mg; capivasertib, or a pharmaceutically acceptable salt thereof; and a pharmaceutically acceptable carrier. In another aspect, the pharmaceutical composition is an oral unit dosage form comprising acalabrutinib, or a pharmaceutically acceptable salt thereof, in an amount of about 100 mg; capivasertib, or a pharmaceutically acceptable salt thereof; and a pharmaceutically acceptable carrier. In another aspect, the pharmaceutical composition is an oral unit dosage form comprising acalabrutinib, or a pharmaceutically acceptable salt thereof, in an amount from about 75 mg to about 125 mg; capivasertib, or a pharmaceutically acceptable salt thereof, in an amount from about 100 mg to about 900 mg; and a pharmaceutically acceptable carrier. In another aspect, the pharmaceutical composition is an oral unit dosage form comprising acalabrutinib, or a pharmaceutically acceptable salt thereof, in an amount from about 75 mg to about 125 mg; capivasertib, or a pharmaceutically acceptable salt thereof, in an amount from about 200 mg to about 800 mg; and a pharmaceutically acceptable carrier. In another aspect, the pharmaceutical composition is an oral unit dosage form comprising acalabrutinib, or a pharmaceutically acceptable salt thereof, in an amount from about 75 mg to about 125 mg; capivasertib, or a pharmaceutically acceptable salt thereof, in an amount from about 300 mg to about 700 mg; and a pharmaceutically acceptable carrier. In another aspect, the pharmaceutical composition is an oral unit dosage form comprising acalabrutinib, or a pharmaceutically acceptable salt thereof, in an amount of about 100 mg; capivasertib, or a pharmaceutically acceptable salt thereof, in an amount from about 100 mg to about 900 mg; and a pharmaceutically acceptable carrier. In another aspect, the pharmaceutical composition is an oral unit dosage form comprising acalabrutinib, or a pharmaceutically acceptable salt thereof, in an amount of about 100 mg; capivasertib, or a pharmaceutically acceptable salt thereof, in an amount from about 200 mg to about 800 mg; and a pharmaceutically acceptable carrier. In another aspect, the pharmaceutical composition is an oral unit dosage form comprising acalabrutinib, or a pharmaceutically acceptable salt thereof, in an amount of about 100 mg; capivasertib, or a pharmaceutically acceptable salt thereof, in an amount from about 300 mg to about 700 mg; and a pharmaceutically acceptable carrier.

The pharmaceutical compositions described above are preferably for use in the treatment of the B-cell malignancies described in this specification. For example, in one aspect, the B-cell malignancy is non-Hodgkin lymphoma. In another aspect, the B-cell malignancy is diffuse large B-cell lymphoma. In another aspect, the B-cell malignancy is activated B-cell (ABC) diffuse large B-cell lymphoma.

V. Kits

The present disclosure further relates, in part, to kits comprising acalabrutinib and capivasertib. The kits include each of acalabrutinib, or a pharmaceutically acceptable salt thereof, and capivasertib, or a pharmaceutically acceptable salt thereof, either alone or in combination in suitable packaging. The kits are for co-administration of acalabrutinib, or a pharmaceutically acceptable salt thereof, and capivasertib, or a pharmaceutically acceptable salt thereof, simultaneously, separately, or sequentially. The kits optionally comprise written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials.

In some embodiments, the kit comprises:

a first pharmaceutical composition comprising a compound of Formula I:

(I)

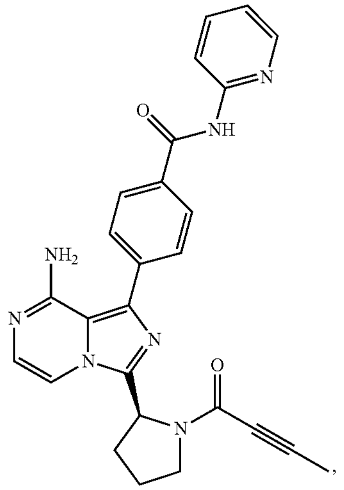

or a pharmaceutically acceptable salt thereof, and a pharmaceutically acceptable carrier;

a second pharmaceutical composition comprising a compound of Formula II:

(II)

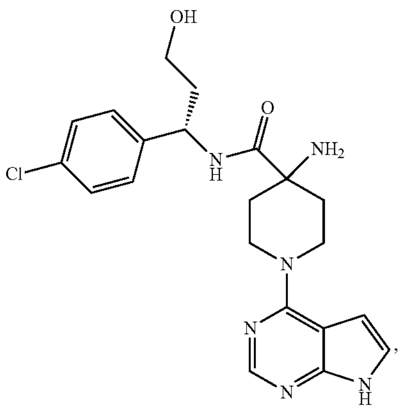

or a pharmaceutically acceptable salt thereof; and a pharmaceutically acceptable carrier.

In some embodiments, the first pharmaceutical composition and the second pharmaceutical composition are each unit dosage forms. In one aspect, the first pharmaceutical composition and the second pharmaceutical composition are each oral unit dosage forms. In another aspect, the first pharmaceutical composition and the second pharmaceutical composition are each oral unit dosage forms, and the first pharmaceutical composition comprises acalabrutinib, or a pharmaceutically acceptable salt thereof, in an amount from about 75 mg to about 125 mg. In another aspect, the first pharmaceutical composition and the second pharmaceutical composition are each oral unit dosage forms, and the first pharmaceutical composition comprises acalabrutinib, or a pharmaceutically acceptable salt thereof, in an amount of about 100 mg.

In some embodiments, the first pharmaceutical composition and the second pharmaceutical composition are each oral unit dosage forms, and the second pharmaceutical composition comprises capivasertib, or a pharmaceutically acceptable salt thereof, in an amount from about 100 mg to about 900 mg. In one aspect, the first pharmaceutical composition and the second pharmaceutical composition are each oral unit dosage forms, and the second pharmaceutical composition comprises capivasertib, or a pharmaceutically acceptable salt thereof, in an amount from about 200 mg to about 800 mg. In another aspect, the first pharmaceutical composition and the second pharmaceutical composition are each oral unit dosage forms, and the second pharmaceutical composition comprises capivasertib, or a pharmaceutically acceptable salt thereof, in an amount from about 300 mg to about 700 mg.

In some embodiments, the first pharmaceutical composition and the second pharmaceutical composition are each oral unit dosage forms, the first pharmaceutical composition comprises acalabrutinib, or a pharmaceutically acceptable salt thereof, in an amount from about 75 mg to about 125 mg, and the second pharmaceutical composition comprises capivasertib, or a pharmaceutically acceptable salt thereof, in an amount from about 100 mg to about 900 mg. In one aspect, the first pharmaceutical composition and the second pharmaceutical composition are each oral unit dosage forms, the first pharmaceutical composition comprises acalabrutinib, or a pharmaceutically acceptable salt thereof, in an amount from about 75 mg to about 125 mg, and the second pharmaceutical composition comprises capivasertib, or a pharmaceutically acceptable salt thereof, in an amount from about 200 mg to about 800 mg. In another aspect, the first pharmaceutical composition and the second pharmaceutical composition are each oral unit dosage forms, the first pharmaceutical composition comprises acalabrutinib, or a pharmaceutically acceptable salt thereof, in an amount from about 75 mg to about 125 mg, and the second pharmaceutical composition comprises capivasertib, or a pharmaceutically acceptable salt thereof, in an amount from about 300 mg to about 700 mg.

In some embodiments, the first pharmaceutical composition and the second pharmaceutical composition are each oral unit dosage forms, the first pharmaceutical composition comprises acalabrutinib, or a pharmaceutically acceptable salt thereof, in an amount of about 100 mg, and the second pharmaceutical composition comprises capivasertib, or a pharmaceutically acceptable salt thereof, in an amount from about 100 mg to about 900 mg. In one aspect, the first pharmaceutical composition and the second pharmaceutical composition are each oral unit dosage forms, the first pharmaceutical composition comprises acalabrutinib, or a pharmaceutically acceptable salt thereof, in an amount of about 100 mg, and the second pharmaceutical composition comprises capivasertib, or a pharmaceutically acceptable salt thereof, in an amount from about 200 mg to about 800 mg. In another aspect, the first pharmaceutical composition and the second pharmaceutical composition are each oral unit dosage forms, the first pharmaceutical composition comprises acalabrutinib, or a pharmaceutically acceptable salt thereof, in an amount of about 100 mg, and the second pharmaceutical composition comprises capivasertib, or a pharmaceutically acceptable salt thereof, in an amount from about 300 mg to about 700 mg.

In some embodiments, acalabrutinib, or a pharmaceutically acceptable salt thereof, and capivasertib, or a pharmaceutically acceptable salt thereof, are provided as a single composition within a container in the kit. In one aspect, therefore, the kit comprises a pharmaceutical composition comprising a compound of Formula I:

(I)

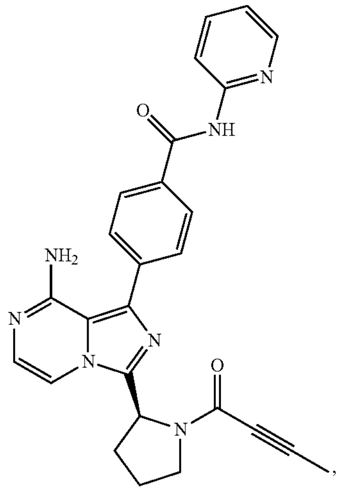

or a pharmaceutically acceptable salt thereof; a compound of Formula II:

(II)

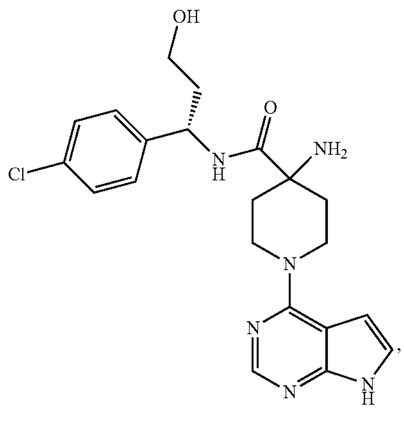

or a pharmaceutically acceptable salt thereof; and a pharmaceutically acceptable carrier. In one aspect, the pharmaceutical composition is a unit dosage form. In another aspect, the pharmaceutical composition is an oral unit dosage form. In another aspect, the pharmaceutical composition is an oral unit dosage form comprising acalabrutinib, or a pharmaceutically acceptable salt thereof, in an amount from about 75 mg to about 125 mg. In another aspect, the pharmaceutical composition is an oral unit dosage form comprising acalabrutinib, or a pharmaceutically acceptable salt thereof, in an amount of about 100 mg.

In some embodiments, the kits may further contain another active pharmaceutical ingredient. In one aspect, acalabrutinib, or a pharmaceutically acceptable salt thereof, and capivasertib, or a pharmaceutically acceptable salt thereof, and another active pharmaceutical ingredient are provided as separate pharmaceutical compositions in separate containers within the kit. In another aspect, acalabrutinib, or a pharmaceutically acceptable salt thereof, and capivasertib, or a pharmaceutically acceptable salt thereof, and the agent are provided as a single composition within a container in the kit. Suitable packaging and additional articles for use (e.g., measuring cup for liquid preparations, foil wrapping to minimize exposure to air, and the like) are known in the art and may be included in the kit. The kits can be provided, marketed and/or promoted to health providers, including physicians, nurses, pharmacists, formulary officials, and the like. The kits may also, in selected embodiments, be marketed directly to the consumer.

In some embodiments, the kits may further comprise a pharmaceutical composition comprising a therapeutically effective amount of cyclophosphamide, doxorubicin, vincristine, prednisone, or combinations thereof. The kit is for co-administration of acalabrutinib, capivasertib, cyclophosphamide, doxorubicin, vincristine, and/or prednisone, either simultaneously or separately.

The kits described above are preferably for use in the treatment of the B-cell malignancies described in this specification. For example, in one aspect, the B-cell malignancy is non-Hodgkin lymphoma. In another aspect, the B-cell malignancy is diffuse large B-cell lymphoma. In another aspect, the B-cell malignancy is activated B-cell (ABC) diffuse large B-cell lymphoma.

VI. Examples

Example 1: In Vitro Pharmacology Study in Diffuse Large B Cell Lymphoma Cell Lines A study was conducted in a panel of diffuse large B-cell lymphoma cell lines to determine if a combination of acalabrutinib and capivasertib could provide benefit, as measured by enhanced inhibition of proliferation and loss of cell viability and indicated by Loewe and HSA synergy scores. In addition, the study further explored the mechanism of action of the combination of acalabrutinib and capivasertib using western blot analysis.

Cell Viability Assays

For the cell viability assays, cells were seeded in 384-well plates and treated with 0.1% DMSO control or increasing concentrations of acalabrutinib, capivasertib, or the combination of acalabrutinib and capivasertib for 72 hours. Cell viability was measured using Cell Titer Glo reagent and readouts were taken using a Tecan plate reader with a 100 ms integration time. Data analysis was carried out using GeneData software version 15. A growth inhibition value less than 1 μM ($GI_{50}$<1 μM) indicates sensitivity.

Treatment of the cells with capivasertib alone inhibited growth of a subset of GCB DLBCL cell lines but had minimal effect on growth in a subset of ABC DLBCL cell lines (see Table EX-1A below). Treatment of the cells with acalabrutinib alone inhibited growth of a subset of ABC DLBCL cell lines but had minimal effect on growth in the subset of GCB DLBCL cell lines tested (see Table EX-1A below).

TABLE EX-1A

| CELL LINE | DISEASE INDICATION | DISEASE SUBTYPE | CAPIVASERTIB $GI_{50}$ (μM) | ACALABRUTINIB $GI_{50}$ (μM) |
|---|---|---|---|---|
| TMD8 | DLBCL | ABC | >3 | 0.025 |
| OCI-LY10 | DLBCL | ABC | >3 | 0.022 |
| U2932 | DLBCL | ABC | >3 | >3 |
| HLY1 | DLBCL | ABC | >3 | >3 |
| OCI-LY3 | DLBCL | ABC | >3 | >3 |
| WILL1 | DLBCL | Int | >3 | >3 |
| WSU-DLCL2 | DLBCL | GCB | 0.06 | >3 |
| SuDHL4 | DLBCL | GCB | 0.71 | >3 |
| Karpas-422 | DLBCL | GCB | 0.20 | >3 |
| OCI-LY19 | DLBCL | GCB | >3 | >3 |
| SuDHL6 | DLBCL | GCB | 0.36 | >3 |

Treatment of the cells with a combination of acalabrutinib and capivasertib, however, resulted in enhanced inhibition of cell growth and loss of cell viability in two ABC DLBCL cell lines, TMD8 and OCI-LY10, as indicated by Loewe's and HSA synergy scores which are reported in Tables EX-1B and EX-1C, respectively. A synergy score more than 3 (>3) indicates potential combination benefit in each synergy model. See, e.g., J. Foucquier et al., "Analysis of drug combinations: current methodological landscape," Pharmacol. Res. Perspect., 3(3) (June 2015); C. J. Lehár et al., "Chemical combination effects predict connectivity in biological systems," Mol. Syst. Biol., 3: 80 (2007); and Keith et al., "Multicomponent therapeutics for networked systems," Nat. Rev. Drug. Discov., 4, 71-78 (2005)

TABLE EX-1B

| LOEWE'S SYNERGY SCORES FOR COMBINATION | | | |
|---|---|---|---|
| CELL LINE | DISEASE INDICATION | DISEASE SUBTYPE | ACALABRUTINIB + CAPIVASERTIB |
| TMD8 | DLBCL | ABC | 4.5 |
| OCI-LY10 | DLBCL | ABC | 3.28 |
| U2932 | DLBCL | ABC | 1.04 |
| HLY1 | DLBCL | ABC | 0 |
| OCI-LY3 | DLBCL | ABC | −0.0453 |
| WILL1 | DLBCL | Int | 0.10 |
| WSU-DLCL2 | DLBCL | GCB | −3.41 |
| SuDHL4 | DLBCL | GCB | −1.10 |
| Karpas-422 | DLBCL | GCB | 0.15 |
| OCI-LY19 | DLBCL | GCB | 0.26 |
| SuDHL6 | DLBCL | GCB | 0.20 |

TABLE EX-1C

| HSA SYNERGY SCORES FOR COMBINATION | | | |
|---|---|---|---|
| CELL LINE | DISEASE INDICATION | DISEASE SUBTYPE | ACALABRUTINIB + CAPIVASERTIB |
| TMD8 | DLBCL | ABC | 9.344 |
| OCI-LY10 | DLBCL | ABC | 3.28 |
| U2932 | DLBCL | ABC | 1.42 |
| HLY1 | DLBCL | ABC | −0.17 |
| OCI-LY3 | DLBCL | ABC | N/A |
| WILL1 | DLBCL | Int | 0.10 |
| SuDHL4 | DLBCL | GCB | 0.26 |
| Karpas-422 | DLBCL | GCB | 0.15 |
| OCI-LY19 | DLBCL | GCB | 0.26 |
| SuDHL6 | DLBCL | GCB | 0.51 |

FIG. 1 depicts Combination Signal Heatmaps (% inhibition of growth signal) for TMD8 cells and OCI-LY10 cells after treatment with a combination of acalabrutinib and capivasertib for 72 hours.

The study indicated that acalabrutinib in combination with capivasertib showed combination benefit and resulted in enhanced loss of cell viability compared to single agents in a subset of human ABC DLBCL cell lines.

Western Blot Analysis

For the western blot analysis, cells were seeded into 6 well plates and treated with 0.1% DMSO, 1 μM capivasertib, 100 nM acalabrutinib, or a combination of 1 μM capivasertib and 100 nM acalabrutinib for two or 24 hours. Cells were then lysed in SDS lysis buffer, centrifuged and protein concentrations estimated. Samples were loaded onto Bis-Tris Novex gels, transferred onto nitrocellulose membranes and probed for phospho-proteins of interest.

FIG. 2 depicts western blots for TMD8 cells and OCI-LY10 cells after treatment with vehicle, acalabrutinib, capivasertib, or a combination of acalabrutinib and capivasertib for 2 hours or 24 hours. Treatment of TMD8 and OCI-LY10 cells with 1 μM capivasertib resulted in increased phosphorylation of AKTS473 and decreased phosphorylation of the downstream substrates PRAS40, GSK3β, FOXO and S6. Treatment of the cells with 100 nM acalabrutinib induced a decrease in phosphorylation of BTK and also inhibited AKT signalling, as indicated by decreased phosphorylation of AKTS473. Treatment of the cells with a combination of capivasertib and acalabrutinib resulted in reduced induction of phosphorylation of AKTS473 and enhanced inhibition of phosphorylation of S6. In addition, the combination lead to induction of cleaved caspase 3 at 24 hours, suggesting enhanced apoptosis in these cell lines.

In this mechanism of action study in TMD8 and OCI-LY10 cells, the combination of acalabrutinib and capivasertib resulted in inhibition of AKT signalling and BTK, and further induced caspase activation.

Example 2: In Vivo Efficacy in a Xenograft Model

A. In Vivo Efficacy in a TMD8 Human ABC-DLBCL Xenograft Model

A study was conducted to evaluate the in vivo efficacy of monotherapy and combination responses of acalabrutinib and capivasertib in a subcutaneous TMD8 human ABC DLBCL xenograft mouse model. Specifically, SCID mice bearing xenograft tumors derived from the TMD8 human activated B-cell (ABC) diffuse large B-cell lymphoma (DLBCL) cell line were evaluated after treatment with either acalabrutinib monotherapy, capivasertib monotherapy, or combination therapy.

TMD8 human ABC-DLBCL tumor cells (5×106/mouse) were implanted subcutaneously in female CB.17 SCID mice. The mice were randomized into groups of five for efficacy based on tumor volume and treated with either vehicle (0.5% MC/0.1% Tween-80), 130 mg/kg capivasertib, 20 mg/kg acalabrutinib, or a combination of acalabrutinib and capivasertib. Capivasertib was formulated in 10% DMSO/25% Kleptose pH=5 and acalabrutinib was formulated in 0.5% MC/0.1% Tween-80. Ten days following tumor cell implantation, all agents were dosed orally according to the schedules listed in Table EX-2A below. Tumor length and width was measured by caliper and tumor volume was calculated using the formula $(\text{length} \times \text{width}^2)*\pi/6$. Plasma pharmacokinetics of acalabrutinib and capivasertib were assessed on day 20 of the efficacy study from micro samples (20 μl) obtained from tail vein live bleeds.

After twenty-four days of treatment, capivasertib monotherapy resulted in 0% tumor growth inhibition (TGI), acalabrutinib monotherapy resulted in 81% tumor growth inhibition (TGI), and the combination of both agents resulted in 98% tumor regression. All treatments were tolerated during the dosing period with maximal body weight loss of 6% over the course of the 24-day study. During the study, steady-state unbound plasma concentrations of acalabrutinib and capivasertib were measured from three mice in the single agent and combination groups at 1, 2, 4, and 8-hour time points. Drug exposure levels of acalabrutinib and capivasertib were similar following oral administration of acalabrutinib and capivasertib single agents or in combination. The overall results are summarized in Table EX-2A below.

TABLE EX-2A

| TREATMENT | DOSE (mg/kg) | SCHEDULE | TGI | REGRESSION | P-VALUE | MAX AVG BODY WEIGHT LOSS |
|---|---|---|---|---|---|---|
| Vehicle* | 0 | BID 10/14 (continuous) × 24 | N/A** | N/A | N/A | 0% |
| Capivasertib | 130 | BID 10/14 4 days on/3 days off × 24 | 0% | N/A | 0.2904 | 2% |
| Acalabrutinib | 20 | BID 10/14 (continuous) × 24 | 81% | N/A | 0.003 | 5% |
| Capivasertib + Acalabrutinib | 130 + 20 | BID 10/14 4 days on/3days off × 24; BID 5 days on/2 days off × 24 | 100% | 98% | <0.0001 | 6% |

*Only n = 4 mice in vehicle group on day 34

**N/A = Not Applicable

FIG. 3 depicts the effect of treatment with vehicle, acalabrutinib, capivasertib, or a combination of acalabrutinib and capivasertib on tumor volume. FIG. 4 depicts the steady state drug exposure after treatment with acalabrutinib, capivasertib, or a combination of acalabrutinib and capivasertib. FIG. 5 depicts the effect of treatment with vehicle, acalabrutinib, capivasertib, or a combination of acalabrutinib and capivasertib on body weight.

Oral treatment with a combination of acalabrutinib and capivasertib resulted in markedly enhanced anti-tumor efficacy leading to complete regression (98%) in a TMD8 human ABC DLBCL xenograft model relative to single agent therapies. All treatments were well tolerated in mice with a maximum body weight loss of 6% observed in the combination treatment group. Pharmacokinetic assessments revealed comparable drug exposure levels for the acalabrutinib and capivasertib single agent and combination groups.

B. In Vivo Efficacy in an OCI-Ly10 Human ABC-DLBCL Xenograft Model

A study was conducted to evaluate the in vivo efficacy of monotherapy and combination responses of acalabrutinib and capivasertib in a subcutaneous OCI-Ly10 human ABC DLBCL xenograft mouse model. Specifically, SCID mice bearing xenograft tumors derived from the OCI-Ly10 human activated B-cell (ABC) diffuse large B-cell lymphoma (DLBCL) cell line were evaluated after treatment with either acalabrutinib monotherapy, capivasertib monotherapy, or combination therapy.

OCI-ly10 human ABC-DLBCL tumor cells (5×106/mouse) were implanted subcutaneously in female CB.17 SCID mice. The mice were randomized into groups of five for efficacy based on tumor volume and treated with either vehicle (0.5% MC/0.1% Tween-80), 130 mg/kg capivasertib, 20 mg/kg acalabrutinib, or a combination of acalabrutinib and capivasertib. Capivasertib was formulated in 10% DMSO/25% Kleptose pH=5 and acalabrutinib was formulated in 0.5% MC/0.1% Tween-80. Nineteen days following tumor cell implantation, all agents were dosed orally according to the schedules listed in Table EX-2B below. Tumor length and width was measured by caliper and tumor volume was calculated using the formula (length×width$^2$)*π/6.

After twenty-five days of treatment, capivasertib monotherapy resulted in 0% tumor growth inhibition (TGI), acalabrutinib monotherapy resulted in 74% tumor growth inhibition (TGI), and the combination of both agents resulted in 78% tumor regression. All treatments were tolerated during the dosing period with maximal body weight loss of 7% over the course of the 25-day study. The overall results are summarized in Table EX-2B below.

TABLE EX-2B

| TREATMENT | DOSE (mg/kg) | SCHEDULE | TGI | REGRESSION | P-VALUE | MAX AVG BODY WEIGHT LOSS |
|---|---|---|---|---|---|---|
| Vehicle* | 0 | BID 10/14 (continuous) × 25 | N/A* | N/A | N/A | 0% |
| Capivasertib | 130 | BID 10/14 4 days on/3 days off × 25 | 0% | N/A | 0.2766 | 3% |
| Acalabrutinib | 20 | BID 10/14 (continuous) × 25 | 74% | N/A | <0.0001 | 2% |
| Capivasertib + Acalabrutinib | 130 + 20 | BID 10/14 4 days on/3days off × 25; BID 5 days on/2 days off × 25 | 100% | 78% | 0.0005 | 7% |

*N/A = Not Applicable

FIG. 6 depicts the effect of treatment with vehicle, acalabrutinib, capivasertib, or a combination of acalabrutinib and capivasertib on tumor volume. FIG. 7 depicts the effect of treatment with vehicle, acalabrutinib, capivasertib, or a combination of acalabrutinib and capivasertib on body weight during the 25-day dosing period.

Oral treatment with a combination of acalabrutinib and capivasertib resulted in markedly enhanced anti-tumor efficacy leading to near complete regression (78%) in a OCI-Ly10 human ABC DLBCL xenograft model relative to single agent therapies. All treatments were well tolerated in mice with a maximum body weight loss of 7% observed in the combination treatment group. Pharmacokinetic assessments revealed comparable drug exposure levels for the acalabrutinib and capivasertib single agent and combination groups.

Example 3: In Vivo Efficacy in Disseminated TMD8-luc2 Human ABC-DLBCL Model

A study was conducted to evaluate the in vivo efficacy of monotherapy and combination responses of acalabrutinib and capivasertib in a disseminated TMD8-luc2 human ABC DLBCL xenograft mouse model. Specifically, SCID mice injected intravenously with a luciferase-tagged TMD8 human activated B-cell (ABC) diffuse large B-cell lymphoma (DLBCL) cell line were evaluated after treatment with either acalabrutinib monotherapy, capivasertib monotherapy, or combination therapy.

TMD8 human ABC-DLBCL tumor cells harboring a luciferase reporter construct (5×106/mouse) were injected intravenously into the tail vein of female CB.17 SCID mice. Tumor burden as measured using the Xenogen IVIS imaging system, body weight, and animal condition were recorded minimally twice weekly for the duration of the study. For Xenogen imaging, mice received an intraperitoneal administration of 150 mg/kg D-Luciferin 10-15 minutes prior to imaging. Imaging of live mice was performed under isoflurane anesthesia and data analyzed using Living Image software (Xenogen). Mice were randomized into groups of five for efficacy based on dorsal and ventral bioluminescence intensity (BLI) and treated with either vehicle (0.5% MC/0.1% Tween-80), 130 mg/kg capivasertib, 20 mg/kg acalabrutinib, or a combination of acalabrutinib and capivasertib. Capivasertib was formulated in 10% DMSO/25% Kleptose pH=5 and acalabrutinib was formulated in 0.5% MC/0.1% Tween-80. Fourteen days following tumor cell injection, all agents were dosed orally according to the schedules listed in Table EX-2A of Example 2. Disseminated tumor burden was measured by Xenogen and study endpoints were determined by the condition of individual animals in which moribound mice were humanely sacrificed.

As depicted in FIG. 8, oral treatment with a combination of acalabrutinib and capivasertib resulted in markedly enhanced survival benefit in a disseminated TMD8-luc2 human ABC DLBCL xenograft mouse model relative to single agent therapies. All treatments were well tolerated in mice until animals reached survival study endpoints.

Example 4: In Vivo Efficacy in Patient-Derived Xenograft Models

A study is conducted to evaluate the in vivo efficacy of monotherapy and combination responses of acalabrutinib and capivasertib in two patient-derived xenograft (PDX) models, a subcutaneous ABC-DLBCL PDX model (LY0257) and a subcutaneous GCB-DLBCL PDX model (LY2214). LY2214 and LY0257 human patient-derived DLBCL primary human tumor fragments (2-3 mm in diameter) will be implanted subcutaneously into female NOD/SCID and B/C nude mice, respectively. The mice will be randomized into groups of five based on tumor volume and treated with either vehicle, acalabrutinib, capivasertib, or a combination of acalabrutinib and capivasertib. Acalabrutinib will be formulated in 0.5% MC+0.1% Tween-80 and capivasertib will formulated in 10% DMSO/25% Kleptose pH=5. When tumors reach sizes between 150 to 300 $mm^3$, vehicle, acalabrutinib, capivasertib, and the combination of acalabrutinib and capivasertib will be dosed orally at the schedules listed in Table EX-2A of Example 2. Tumor volumes will be measured twice per week in two dimensions using a caliper, and the volume will be expressed in $mm^3$ using the formula: "V=(L×W×W)/2, where V is tumor volume, L is tumor length (the longest tumor dimension), and W is tumor width (the longest tumor dimension perpendicular to L).

Example 5: RNAseq Study

An RNAseq study is conducted on TMD8 cells treated with acalabrutinib, capivasertib, or a combination of acalabrutinib and capivasertib. Specifically, TMD8 cells are seeded into six well plates and treated with 0.1% DMSO, 1 μM capivasertib, 100 nM acalabrutinib, or a combination of 1 μM capivasertib and 100 nM acalabrutinib for six or 24 hours. Cells pellets are then made and RNA isolated. RNA samples are sent to Novogene for cDNA library generation, and mRNA sequencing (RNA-seq). RNAseq data is analyzed using inhouse pipeline, quantifying gene expression using Salmon method (Patro R, 2017). Differential expression analysis is carried out using DESeq2 (Love M I, 2014). Enrichment analysis is carried using GSVA (Hänzelmann S, 2013).

Example 6: In-Vivo Pharmacodynamic Study

A pharmacodynamic study is conducted to evaluate monotherapy and combination responses of acalabrutinib and capivasertib. TMD8 human ABC-DLBCL tumor cells (5×106/mouse) will be implanted subcutaneously in female CB.17 SCID mice. The mice will be randomized into groups of three for evaluation based on when tumor volumes reach approximately 300 to 600 $mm^3$ and then will be treated with either a single acute dose or multiple doses of either vehicle (0.5% MC/0.1% Tween-80), 20 mg/kg acalabrutinib, 130 mg/kg capivasertib, or the combination at 2, 8, 14, 24-hour time points. The pharmacodynamic assessment of acalabrutinib and capivasertib will include pS6, pBTK, pAKT, p4EBP1, and pPLCγ2.

Example 7: Clinical Study of Combination to Treat Relapsed/Refractory DLBCL Lymphoma A Phase 1/2, single-arm, open-label, proof-of-concept study is conducted to evaluate the combination of acalabrutinib with capivasertib for treating patients with relapsed/refractory DLBCL. The study will assess the clinical potential of a dual BTK and AKT inhibition approach by evaluating the safety, pharmacokinetics, pharmacodynamics, and efficacy of acalabrutinib and capivasertib combination therapy in treating relapsed/refractory DLBCL.

Study Objectives

The objectives of Part 1 of the clinical study include determining a dose and schedule for capivasertib in combination with acalabrutinib 100 mg BID for evaluation in Part 2 of the clinical study. The primary objective of Part 2 of the clinical study is to evaluate the safety of acalabrutinib and capivasertib when co-administered. Secondary objectives of Part 2 of the clinical study include evaluating the pharmacokinetics, pharmacodynamics, and clinical activity of acalabrutinib and capivasertib when co-administered.

Safety parameters that will be evaluated include, but are not limited to, type, frequency, severity, and relationship to study drug of any treatment-emergent adverse events (TEAEs) or abnormalities of laboratory tests, serious adverse events (SAEs), dose limiting toxicities (DLTs), and adverse events (AEs) leading to discontinuation of study drug(s).

The plasma pharmacokinetics of acalabrutinib and capivasertib will be characterized using noncompartmental analysis and the following pharmacokinetic parameters will be calculated, whenever possible, from plasma concentrations of analytes: (1) $AUC_{(0\text{-}last)}$: area under the plasma concentration-time curve calculated using linear trapezoidal summation from time 0 to time last, where "last" is the time of the last measurable concentration; $AUC_{(0\text{-}inf)}$: area under the plasma concentration-time curve from 0 to infinity, calculated using the formula: $AUC_{(0\text{-}inf)}$>=$AUC_{(0\text{-}last)}$+$C_{(last/\lambda z)}$, where $\lambda_z$ is the apparent terminal elimination rate constant; $C_{max}$: maximum observed plasma concentration; $T_{max}$: time of the maximum plasma concentration (obtained without interpolation); $t_{1/2}$: terminal elimination half-life (whenever possible); $\lambda_z$: terminal elimination rate constant (whenever possible); CL/F: oral clearance; $V_z$/F: oral volume of distribution.

The pharmacodynamic assessment of acalabrutinib and capivasertib will include (1) measuring the occupancy of BTK by acalabrutinib in peripheral blood mononuclear cells (PBMCs) with the aid of an acalabrutinib analogue probe, (2) evaluating the effect of acalabrutinib and capivasertib on biologic markers of B-cell function and/or AKT inhibition in PBMCs and/or tumor tissue, and (3) assessing the effect of acalabrutinib and capivasertib on circulating tumor DNA (ctDNA). Cell populations and immunological markers will be monitored for effect of treatment, which may include, but are not limited to, leukocyte or lymphocyte subsets (e.g., T, B and natural killer [NK] cells) and their activation states. Additional markers may include Ki67, pS6, pBTK, pAKT, pPRAS40, pGSK3β, p4EBP1, FOX3, and pPLCγ2.

Clinical activity of acalabrutinib and capivasertib will be evaluated by measuring overall response rate (ORR=CR+PR), complete response (CR) rate, duration of response (DOR), progression-free survival (PFS), and overall survival (OS).

The study objectives and endpoints are summarized in Table EX-7A below.

TABLE EX-7A

| OBJECTIVES AND ENDPOINTS | |
|---|---|
| PRIMARY OBJECTIVE: | ENDPOINTS/VARIABLES: |
| To evaluate the safety of capivasertib and acalabrutinib for the treatment of relapsed/refractory DLBCL | Type, frequency, severity, and relationship to study treatment(s) of any treatment-emergent adverse events (TEAEs) or abnormalities of laboratory tests, serious adverse events |

TABLE EX-7A-continued

| OBJECTIVES AND ENDPOINTS | |
|---|---|
| | (SAEs), dose-limiting toxicities (DLTs), or adverse events (AEs) leading to discontinuation of study treatment(s). |
| SECONDARY OBJECTIVE: | ENDPOINTS/VARIABLES: |
| To evaluate the clinical activity of capivasertib and acalabrutinib for the treatment of relapsed/refractory DLBCL<br>To assess the pharmacokinetics of capivasertib and acalabrutinib | Clinical activity endpoints:<br>Overall response rate (ORR)<br>Duration of response (DOR)<br>Progression-free survival (PFS)<br>Overall survival (OS)<br>Standard and appropriate pharmacokinetic parameters |
| Exploratory objectives: | Endpoints/variable: |
| Pharmacodynamic and pharmacokinetic-pharmacokinetic effects of the study treatment(s) in surrogate tissues and/or biopsies (when available).<br>Measurable residual disease (MRD) assessments and longitudinal monitoring of MRD.<br>Investigate markers associated with sensitivity or innate or acquired resistance to the study treatment(s) that may be observed in circulating tumour DNA (ctDNA), tumour tissue or serum/plasma. These may be protein, mRNA or DNA markers.<br>Collect for long-term storage and/or analyse tumour biopsies and surplus plasma/serum or tissue (including patient-specific archival tumour tissue, if available) for potential future exploratory research into factors that may influence development of lymphoma and/or response to study treatments (where response is defined broadly to include distribution, efficacy, pharmacodynamic activity, tolerability, or safety). This may include the analysis of tumour and circulating biomarkers, such as DNA, mRNA, proteins or metabolites. | Serum/plasma concentration of cytokines, AKT and BTK occupancy and pathway analysis from peripheral blood mononuclear cells will be measured pre- and postdosing. Tumour biopsy immunohistochemistry for BTK and other markers (e.g., PTEN loss), as appropriate, will be measured before and after dosing. The relationship of the pharmacodynamic biomarkers to study drug exposure levels may also be conducted.<br>Correlations of MRD detectability using DNA based methods to response depth and DOR, PFS and OS.<br>Longitudinal analysis of genomic markers of the AKT and BTK pathways, as well as disease specific markers and relationship to study drug exposure.<br>Correlative analysis with treatment effects to determine if any recurrent biomarkers can predict response, as well as, any relationship to study drug exposure levels. |

Study Design

The study is an exploratory, multicenter, open-label, non-randomized Phase I platform study to be conducted at approximately 25 sites.

Number of Subjects

The study will enroll up to 21 evaluable subjects.

Dosage Form and Strength

Acalabrutinib drug product is provided as hard gelatin capsules containing 100 mg of acalabrutinib for oral administration.

Capivasertib drug product is provided as film-coated tablets containing either 160 mg or 200 mg of capivasertib for oral administration.

Dose Regimen and Route of Administration

Acalabrutinib and capivasertib are administered orally twice daily with 8 ounces (approximately 240 mL) of water (avoid grapefruit juice or Seville orange juice due to potential inhibition of CYP3A). Doses are administered 12 hours apart (a window of ±1 hour is allowed) at approximately the same times each day. Subjects will fast (water to drink only) from at least two hours before taking a dose to at least one hour post-dose for all doses. The acalabrutinib capsules and capivasertib tablets are taken concomitantly and are swallowed intact. Acalabrutinib is taken every day while capivasertib is taken on a schedule of 4 days on, 3 days off.

Inclusion Criteria

To be eligible for the study, subjects must meet the following inclusion criteria:

1. Diagnosis of relapsed/refractory DLBCL or aggressive lymphoma (i.e., B-cell NHL) and with histology based on criteria established by the World Health Organization (WHO). Eligible histologies are:
   (a) DLBCL (de novo and transformed including Richter syndrome)
   (b) T-cell/histiocyte-rich large B-cell lymphoma
   (c) primary cutaneous DLBCL
   (d) leg-type primary cutaneous DLBCL
   (e) Epstein-Barr virus-positive ($EBV^+$) DLBCL
   (f) DLBCL associated with chronic inflammation
   (g) primary mediastinal (thymic) large B-cell lymphoma
   (h) intravascular large B-cell lymphoma
   (i) anaplastic lymphoma kinase-positive ($ALK^+$) large B-cell lymphoma
   (j) high-grade B-cell lymphoma with rearrangements of MYC and BCL2 or of BCL6 and MYC
2. Must have previously received rituximab, cyclophosphamide, doxorubicin hydrochloride (hydroxydaunorubicin), vincristine sulfate, and prednisone (i.e., R-CHOP) or equivalent regimen, and high-dose therapy with stem-cell rescue, or who are ineligible for high-dose chemotherapy with stem-cell rescue and/or chimeric antigen receptor (CAR) T-cell therapy. Ineligibility for high-dose therapy with stem cell rescue and/or CAR T-cell therapy will be determined by the investigator (includes subjects who decline to undergo transplant).

3. Adequate haematologic function defined as:
   (a) ANC≥1000 cells/$mm^3$ ($1.0\times10^9$/L).
   (b) Platelet count ≥100,000 cells/$mm^3$ ($100\times10^9$/L) or ≥50,000 cells/$mm^3$ ($50\times10^9$/L) in presence of bone marrow or spleen involvement. Platelet count entry requirement must be met without transfusion support.
   (c) Hemoglobin ≥9 g/dL.
4. Willing and able to participate in all required evaluations and procedures in this study protocol including swallowing capsules/tablets without difficulty.
5. Women should be using highly effective contraceptive measures, should not be breastfeeding and must have a negative pregnancy test (urine or serum) before start of dosing if of child-bearing potential or must have evidence of nonchildbearing potential by fulfilling one of the following criteria at screening:
   (a) Postmenopausal women, defined as either women aged >50 years and amenorrheic for ≥12 months following cessation of all exogenous hormonal treatments, or, women under 50 years old who have been amenorrheic for ≥12 months following the cessation of exogenous hormonal treatments, and have serum follicle-stimulating hormone (FSH) and luteinizing hormone (LH) levels in the postmenopausal range for the institution.
   (b) Documentation of irreversible surgical sterilization by hysterectomy, bilateral oophorectomy or bilateral salpingectomy but not tubal ligation.
   (c) Medically confirmed, irreversible premature ovarian failure.

Women who are sexually active and of childbearing potential must be willing to use 2 forms of contraception from the time of screening and continue for 2 days after the last dose of acalabrutinib and 4 weeks after the last dose of capivasertib. Women must also refrain from egg cell donation and breastfeeding during this same time.

6. Men must use a condom (with spermicide) during the study, and for 16 weeks after the last dose of capivasertib, with all sexual partners. Men must not donate sperm during this same time. If not done previously, storage of sperm before receiving capivasertib will be advised to male subjects with a desire to have children.

Exclusion Criteria

Subjects are not eligible for the study if the meet any of the following exclusion criteria:

1. Any of the following cardiac criteria at screening:
   (a) Mean resting corrected QT interval (QTc)>470 ms obtained from 3 consecutive electrocardiograms (ECGs).
   (b) Any clinically important abnormalities in rhythm, conduction or morphology of resting ECG (e.g., complete left bundle branch block or third degree heart block).
   (c) Any factors that increase the risk of QTc prolongation or risk of arrhythmic events such as heart failure, hypokalemia, potential for Torsades de Pointes, congenital long QT syndrome, family history of long QT syndrome or unexplained sudden death under 40 years of age or any concomitant medication known to prolong the QT interval.
   (d) Experience of any of the following procedures or conditions in the preceding 6 months: coronary artery bypass graft, angioplasty, vascular stent, myocardial infarction, angina pectoris, congestive heart failure New York Heart Association (NYHA) Class ≥2.
   (e) Uncontrolled hypotension—systolic blood pressure <90 mmHg and/or diastolic blood pressure <50 mmHg.
   (f) Cardiac ejection fraction outside institutional range of normal or <50% (whichever is higher) as measured by echocardiogram (or multiple-gated acquisition [MUGA] scan if an echocardiogram cannot be performed or is inconclusive).
2. Clinically significant abnormalities of glucose metabolism as defined by any of the following at screening:
   (a) Subjects with diabetes mellitus type 1 or diabetes mellitus type 2 requiring insulin treatment.
   (b) HbA1c≥8.0% (63.9 mmol/mol).
3. Inadequate renal function as demonstrated by creatinine >1.5×ULN concurrent with creatinine clearance <50 mL/min (measured or calculated by Cockcroft and Gault equation); confirmation of creatinine clearance is only required when creatinine is >1.5×ULN.
4. Presence of central nervous system (CNS) lymphoma or leptomeningeal disease.
5. Current refractory nausea and vomiting, malabsorption syndrome, disease significantly affecting gastrointestinal (GI) function, resection of the stomach, extensive small bowel resection that is likely to affect absorption, symptomatic inflammatory bowel disease, partial or complete bowel obstruction, or gastric restrictions and bariatric surgery, such as gastric bypass.
6. Known to have tested positive for human immunodeficiency virus (HIV) and requires treatment with restricted medications.
7. Potent inhibitors or inducers of CYP3A4 within 2 weeks (3 weeks for St John's wort) before the first dose of capivasertib and within 7 days before the first dose of acalabrutinib, or sensitive substrates of CYP3A4, CYP2C9 and/or CYP2D6 with a narrow therapeutic window within 1 week before the first dose of capivasertib.
8. Requires treatment with proton-pump inhibitors (eg, omeprazole, esomeprazole, lansoprazole, dexlansoprazole, rabeprazole, or pantoprazole). Subjects receiving proton-pump inhibitors who switch to H2-receptor antagonists or antacids are eligible for enrolment to this study.
9. Major surgical procedure within 28 days before first dose of study treatment. Note: If a subject had major surgery, they must have recovered adequately from any toxicity and/or complications from the intervention before the first dose of study treatment. For local procedures (eg, placement of a systemic port and biopsies) discussion with the Medical Monitor is required to assess the subject's risk for severe bleeding.

The clinical data will confirm that co-administration of acalabrutinib and capivasertib provides unexpected improvement in the treatment of DLBCL (e.g., de novo DLBCL, relapsed/refractory DLBCL, and/or transformed DLBCL) relative to mono-therapeutic administration of acalabrutinib and capivasertib alone.

This written description uses examples to disclose the invention and to enable any person skilled in the art to practice the invention, including making and using any of the disclosed salts, substances, or compositions, and performing any of the disclosed methods or processes. The patentable scope of the invention is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims. While preferred embodiments of the invention are shown and described in this specification, such embodiments are provided by way of example only and are not intended to otherwise limit the scope of the invention. Various alternatives to the described embodiments of the invention may be employed in practicing the invention. Section headings as used in this section and the entire disclosure are not intended to be limiting.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:

1. A method of treating a B-cell malignancy in a human subject in need thereof, comprising administering to the human subject a first amount of a compound of Formula I:

(I)

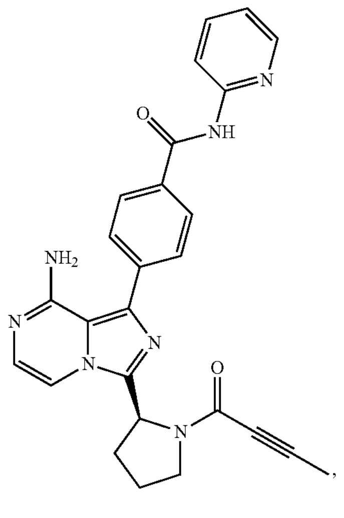

or a pharmaceutically acceptable salt thereof, and a second amount of a compound of Formula II:

(II)

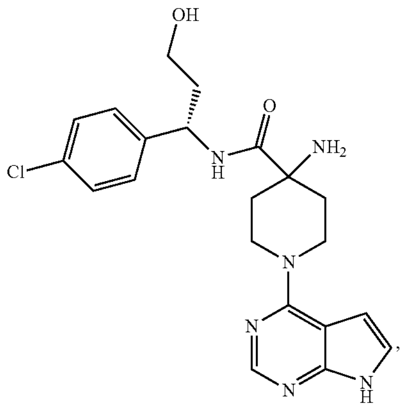

or a pharmaceutically acceptable salt thereof, wherein the first amount and the second amount together comprise a therapeutically effective amount.

2. The method of claim 1, wherein the B-cell malignancy is non-Hodgkin lymphoma.

3. The method of claim 1, wherein the B-cell malignancy is selected from the group consisting of mantle cell lymphoma; follicular lymphoma; de novo diffuse large B-cell lymphoma; transformed diffuse large B-cell lymphoma; T-cell/histiocyte-rich large B-cell lymphoma; primary cutaneous diffuse large B-cell lymphoma; leg-type primary cutaneous diffuse large B-cell lymphoma; Epstein-Barr virus-positive diffuse large B-cell lymphoma; diffuse large B-cell lymphoma associated with chronic inflammation; primary mediastinal large B-cell lymphoma; intravascular large B-cell lymphoma; anaplastic lymphoma kinase-positive (ALK+) large B-cell lymphoma; and high-grade B-cell lymphoma with rearrangements of MYC and BCL2 or of BCL6 and MYC.

4. The method of claim 1, wherein the B-cell malignancy is selected from the group consisting of de novo diffuse large B-cell lymphoma; transformed diffuse large B-cell lymphoma; T-cell/histiocyte-rich large B-cell lymphoma; primary cutaneous diffuse large B-cell lymphoma; leg-type primary cutaneous diffuse large B-cell lymphoma; Epstein-Barr virus-positive diffuse large B-cell lymphoma; diffuse large B-cell lymphoma associated with chronic inflammation; primary mediastinal large B-cell lymphoma; intravascular large B-cell lymphoma; anaplastic lymphoma kinase-positive (ALK+) large B-cell lymphoma; and high-grade B-cell lymphoma with rearrangements of MYC and BCL2 or of BCL6 and MYC.

5. The method of claim 1, wherein the B-cell malignancy is diffuse large B-cell lymphoma.

6. The method of claim 5, wherein the diffuse large B-cell lymphoma is selected from the group consisting of de novo diffuse large B-cell lymphoma, relapsed/refractory diffuse large B-cell lymphoma, and transformed diffuse large B-cell lymphoma.

7. The method of claim 5, wherein the diffuse large B-cell lymphoma is selected from the group consisting of germinal center B-cell (GCB) diffuse large B-cell lymphoma and activated B-cell (ABC) diffuse large B-cell lymphoma.

8. The method of claim 5, wherein the diffuse large B-cell lymphoma is activated B-cell (ABC) diffuse large B-cell lymphoma.

9. The method of claim 5, wherein the human subject has previously received at least one prior chemo-immunotherapy for the diffuse large B-cell lymphoma.

10. The method of claim 1 wherein the method comprises orally administering to the human subject the compound of Formula I, or a pharmaceutically acceptable salt thereof, and the compound of Formula II, or a pharmaceutically acceptable salt thereof.

11. The method of claim 10, wherein the compound of Formula I, or a pharmaceutically acceptable salt thereof, is orally co-administered to the human subject with the compound of Formula II, or a pharmaceutically acceptable salt thereof.

12. The method of claim 10, wherein the compound of Formula I, or a pharmaceutically acceptable salt thereof, is orally administered to the human subject before or after the compound of Formula II, or a pharmaceutically acceptable salt thereof.

13. The method of claim 1, wherein the first amount of the compound of Formula I, or a pharmaceutically acceptable salt thereof, administered to the human subject is from about 75 mg to about 225 mg daily.

14. The method of claim 1, wherein the first amount of the compound of Formula I, or a pharmaceutically acceptable salt thereof, administered to the human subject is about 100 mg once daily.

15. The method of claim 1, wherein the first amount of the compound of Formula I, or a pharmaceutically acceptable salt thereof, administered to the human subject is about 100 mg twice daily.

16. The method of claim 1, wherein the compound of Formula I, or a pharmaceutically acceptable salt thereof, is orally administered to the human subject under a continuous dosing schedule.

17. The method of claim 1, wherein the compound of Formula II, or a pharmaceutically acceptable salt thereof, is orally administered to the human subject under an intermittent dosing schedule.

18. The method of claim 1, wherein:

the compound of Formula I, or a pharmaceutically acceptable salt thereof, is orally administered to the human subject under a continuous dosing schedule; and the compound of Formula II, or a pharmaceutically acceptable salt thereof, is orally administered to the human subject under an intermittent dosing schedule.

19. The method of claim 1, wherein the second amount of the compound of Formula II, or a pharmaceutically acceptable salt thereof, administered to the human subject is from about 50 mg twice daily to about 900 mg twice daily.

20. A pharmaceutical composition comprising:

a compound of Formula I:

(I)

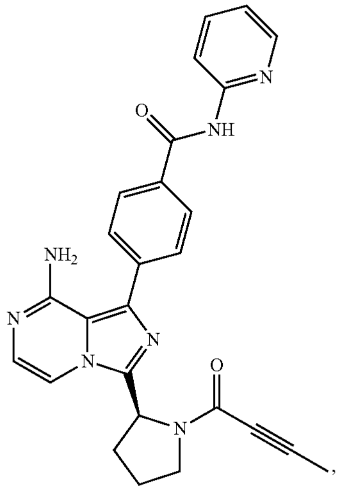

or a pharmaceutically acceptable salt thereof;

a compound of Formula II:

(II)

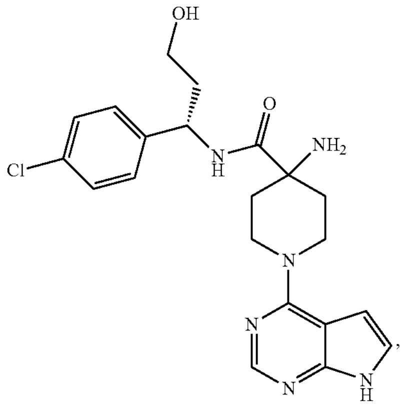

or a pharmaceutically acceptable salt thereof; and a pharmaceutically acceptable carrier.

21. A kit comprising:

a first pharmaceutical composition comprising a compound of Formula I:

(I)

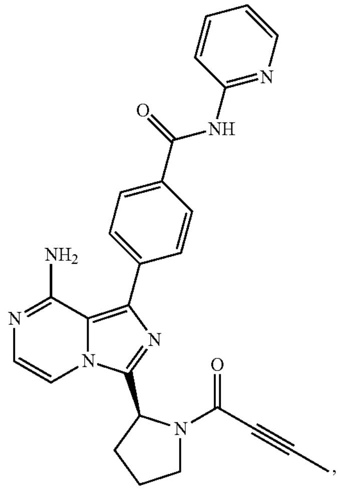

or a pharmaceutically acceptable salt thereof, and a pharmaceutically acceptable carrier;

a second pharmaceutical composition comprising a compound of Formula II:

(II)

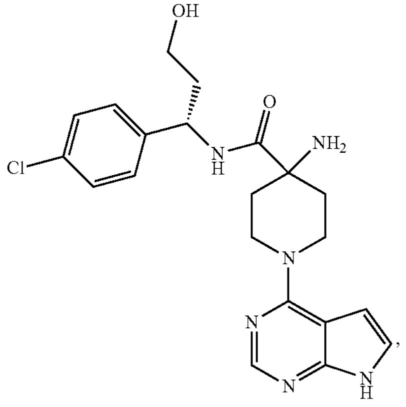

or a pharmaceutically acceptable salt thereof, and a pharmaceutically acceptable carrier.

22. The method of claim 8, wherein the activated B-cell (ABC) diffuse large B-cell lymphoma is relapsed/refractory activated B-cell (ABC) diffuse large B-cell lymphoma.

* * * * *